(12) United States Patent
Hodos et al.

(10) Patent No.: US 8,028,698 B2
(45) Date of Patent: Oct. 4, 2011

(54) BREATHING MASK

(75) Inventors: Valentine A. Hodos, Cleveland, OH (US); Neal J. Curran, Lakewood, OH (US); Christopher H. Delgado, Glendale, AZ (US)

(73) Assignee: Invacare Corporation, Elyria, OH (US)

( * ) Notice: Subject to any disclaimer, the term of this patent is extended or adjusted under 35 U.S.C. 154(b) by 976 days.

(21) Appl. No.: 11/856,131

(22) Filed: Sep. 17, 2007

(65) Prior Publication Data

US 2008/0066761 A1 Mar. 20, 2008

Related U.S. Application Data

(60) Provisional application No. 60/826,015, filed on Sep. 18, 2006.

(51) Int. Cl.
*A62B 18/02* (2006.01)
*A62B 18/08* (2006.01)

(52) U.S. Cl. ............................ 128/206.21; 128/206.24

(58) Field of Classification Search ............ 128/206.21, 128/206.24, 206.27, 206.28, 207.11, 205.25
See application file for complete search history.

(56) References Cited

U.S. PATENT DOCUMENTS

| | | |
|---|---|---|
| 781,516 A | 1/1905 | Guthrie, Jr. |
| 812,706 A | 2/1906 | Warbasse |
| 844,097 A | 2/1907 | Caldwell |
| 1,048,491 A | 12/1912 | Bulcher |
| 1,081,745 A | 12/1913 | Johnston et al. |
| 1,192,186 A | 7/1916 | Greene |
| 1,206,045 A | 11/1916 | Smith |
| 1,632,449 A | 6/1927 | McKesson |
| 1,635,275 A | 7/1927 | Johnson |
| 1,653,572 A | 12/1927 | Jackson |
| 1,926,027 A | 9/1933 | Biggs |
| 2,123,353 A | 7/1938 | Catt |
| 2,241,535 A | 5/1941 | Boothby et al. |
| 2,248,477 A | 7/1941 | Lombard |
| 2,254,854 A | 9/1941 | O'Conell |
| 2,317,608 A | 4/1943 | Heidbrink |
| 2,371,965 A | 3/1945 | Lehmberg |
| 2,376,871 A | 5/1945 | Fink |
| 2,415,846 A | 2/1947 | Randall |
| 2,438,058 A | 3/1948 | Kincheloe |
| 2,578,621 A | 12/1951 | Yant |
| 2,765,788 A | 10/1956 | Raiche |
| 2,939,458 A | 6/1960 | Lundquist |

(Continued)

FOREIGN PATENT DOCUMENTS

AU 32914/95 2/1996

(Continued)

OTHER PUBLICATIONS

Search Report from European Application No. 07116625.0 dated Sep. 3, 2009. PCT Search report and Written Opinion from PCT/US2004/016192, pp. 1-22, dated Dec. 9, 2004.
PCT Search Report from PCT/US2003/008773, pp. 1-9, mailed Dec. 4, 2003.
Communication pursuant to Article 96(2) from EP Application No. 03745562.3-2310, dated Apr. 15, 2005.

(Continued)

*Primary Examiner* — Kristen Matter
(74) *Attorney, Agent, or Firm* — Calfee, Halter & Griswold LLP

(57) ABSTRACT

Breathing mask assemblies that include adjustable forehead supports are disclosed herein. In one embodiment, a forehead support is adjustably coupled to a central or main body of the breathing mask. A clamp is configured to lock the position of the forehead support relative to the central body and to lock forehead support at multiple different positions. In one exemplary embodiment, the forehead support may be locked at any position along a path of travel between a first position and a second position.

10 Claims, 24 Drawing Sheets

U.S. PATENT DOCUMENTS

| | | |
|---|---|---|
| 3,013,556 A | 12/1961 | Galleher, Jr. |
| 3,182,659 A | 5/1965 | Blout |
| 3,189,027 A | 6/1965 | Bartlett, Jr. |
| 3,193,624 A | 7/1965 | Webb et al. |
| 3,238,943 A | 3/1966 | Holley |
| 3,315,674 A | 4/1967 | Bloom et al. |
| 3,330,273 A | 7/1967 | Bennett |
| 3,330,274 A | 7/1967 | Bennett |
| 3,362,420 A | 1/1968 | Blackburn et al. |
| 3,363,833 A | 1/1968 | Laerdal |
| 3,556,122 A | 1/1971 | Laerdal |
| 3,580,051 A | 5/1971 | Blevins |
| 3,700,000 A | 10/1972 | Hesse et al. |
| 3,720,235 A | 3/1973 | Schrock |
| 3,725,953 A | 4/1973 | Johnson et al. |
| 3,779,164 A | 12/1973 | Study |
| 3,982,532 A | 9/1976 | Halldin et al. |
| 4,077,404 A | 3/1978 | Elam |
| 4,167,185 A | 9/1979 | Lewis |
| 4,226,234 A | 10/1980 | Gunderson |
| 4,245,632 A | 1/1981 | Houston |
| 4,263,908 A | 4/1981 | Mizerak |
| 4,266,540 A | 5/1981 | Panzik et al. |
| 4,304,220 A | 12/1981 | Curtin |
| 4,328,797 A | 5/1982 | Rollins, III et al. |
| 4,347,205 A | 8/1982 | Stewart |
| 4,354,488 A | 10/1982 | Bartos |
| 4,402,316 A | 9/1983 | Gadberry |
| 4,412,537 A | 11/1983 | Tiger |
| 4,467,799 A | 8/1984 | Steinberg |
| 4,522,639 A | 6/1985 | Ansite et al. |
| 4,558,710 A | 12/1985 | Eichler |
| 4,559,940 A | 12/1985 | McGinnis |
| 4,616,647 A | 10/1986 | McCreadie |
| 4,622,964 A | 11/1986 | Flynn |
| 4,655,213 A | 4/1987 | Rapoport et al. |
| 4,665,570 A | 5/1987 | Davis |
| 4,671,271 A | 6/1987 | Bishop et al. |
| 4,677,975 A | 7/1987 | Edgar et al. |
| 4,677,977 A | 7/1987 | Wilcox |
| H397 H | 1/1988 | Stark |
| 4,739,755 A | 4/1988 | White et al. |
| 4,770,169 A | 9/1988 | Schmoegner et al. |
| 4,774,941 A | 10/1988 | Cook |
| 4,782,832 A | 11/1988 | Trimble et al. |
| 4,799,477 A | 1/1989 | Lewis |
| 4,809,692 A | 3/1989 | Nowacki et al. |
| 4,819,629 A | 4/1989 | Jonson |
| 4,821,713 A | 4/1989 | Bauman |
| 4,841,953 A | 6/1989 | Dodrill |
| 4,848,334 A | 7/1989 | Bellm |
| 4,848,366 A | 7/1989 | Aita et al. |
| 4,907,584 A | 3/1990 | McGinnis |
| 4,910,806 A | 3/1990 | Baker et al. |
| 4,919,128 A | 4/1990 | Kopala et al. |
| 4,938,210 A | 7/1990 | Shene |
| 4,938,212 A | 7/1990 | Snook et al. |
| 4,944,310 A | 7/1990 | Sullivan |
| 4,971,051 A | 11/1990 | Toffolon |
| 4,986,269 A | 1/1991 | Hakkinen |
| 4,989,596 A | 2/1991 | Macris et al. |
| 4,989,599 A | 2/1991 | Carter |
| 5,005,568 A | 4/1991 | Loescher et al. |
| 5,005,571 A | 4/1991 | Dietz |
| 5,038,776 A | 8/1991 | Harrison et al. |
| 5,042,473 A | 8/1991 | Lewis |
| 5,046,200 A | 9/1991 | Feder |
| 5,063,922 A | 11/1991 | Hakkinen |
| 5,069,205 A | 12/1991 | Urso |
| 5,109,839 A | 5/1992 | Blasdell et al. |
| 5,109,840 A | 5/1992 | Daleiden |
| 5,117,819 A | 6/1992 | Servidio et al. |
| 5,121,745 A | 6/1992 | Israel |
| 5,133,347 A | 7/1992 | Huennebeck |
| 5,140,980 A | 8/1992 | Haughey et al. |
| 5,140,982 A | 8/1992 | Bauman |
| 5,159,938 A | 11/1992 | Laughlin |
| 5,178,138 A | 1/1993 | Walstrom et al. |
| D333,015 S | 2/1993 | Farmer et al. |
| 5,199,424 A | 4/1993 | Sullivan et al. |
| 5,231,983 A | 8/1993 | Matson et al. |
| 5,233,978 A | 8/1993 | Callaway |
| 5,265,595 A | 11/1993 | Rudolph |
| 5,279,289 A | 1/1994 | Kirk |
| 5,280,784 A | 1/1994 | Kohler |
| 5,311,862 A | 5/1994 | Blasdell et al. |
| 5,322,057 A | 6/1994 | Raabe et al. |
| 5,343,878 A | 9/1994 | Scarberry et al. |
| 5,357,951 A | 10/1994 | Ratner |
| 5,372,130 A | 12/1994 | Stern et al. |
| 5,388,571 A | 2/1995 | Roberts et al. |
| 5,404,871 A | 4/1995 | Goodman et al. |
| 5,419,318 A | 5/1995 | Tayebi |
| 5,429,126 A | 7/1995 | Bracken |
| 5,429,683 A | 7/1995 | LeMitouard |
| 5,431,158 A | 7/1995 | Tirotta |
| 5,433,193 A | 7/1995 | Sanders et al. |
| 5,438,981 A | 8/1995 | Starr et al. |
| 5,441,046 A | 8/1995 | Starr et al. |
| 5,477,852 A | 12/1995 | Landis et al. |
| 5,479,920 A | 1/1996 | Piper et al. |
| 5,488,948 A | 2/1996 | Dubruille et al. |
| 5,492,116 A | 2/1996 | Scarberry et al. |
| 5,501,214 A | 3/1996 | Sabo |
| 5,509,404 A | 4/1996 | Lloyd et al. |
| 5,517,986 A | 5/1996 | Starr et al. |
| 5,538,000 A | 7/1996 | Rudolph |
| 5,540,223 A | 7/1996 | Starr et al. |
| 5,546,938 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,570,682 A | 11/1996 | Johnson |
| 5,570,689 A | 11/1996 | Starr et al. |
| D377,089 S | 12/1996 | Starr et al. |
| 5,592,938 A | 1/1997 | Scarberry et al. |
| 5,608,647 A | 3/1997 | Rubsamen et al. |
| 5,642,730 A | 7/1997 | Baran |
| 5,647,355 A | 7/1997 | Starr et al. |
| 5,647,357 A | 7/1997 | Barnett et al. |
| 5,649,532 A | 7/1997 | Griffiths |
| 5,649,533 A | 7/1997 | Oren |
| 5,655,520 A | 8/1997 | Howe et al. |
| 5,655,527 A | 8/1997 | Scarberry et al. |
| 5,657,752 A | 8/1997 | Landis et al. |
| 5,662,101 A | 9/1997 | Ogden et al. |
| 5,666,946 A | 9/1997 | Langenback |
| 5,673,690 A | 10/1997 | Tayebi et al. |
| D385,960 S | 11/1997 | Rudolph |
| 5,685,296 A | 11/1997 | Zdrojkowski et al. |
| 5,690,102 A | 11/1997 | Bertheau et al. |
| D388,873 S | 1/1998 | Richards et al. |
| 5,715,814 A | 2/1998 | Ebers |
| 5,724,965 A | 3/1998 | Handke et al. |
| 5,738,094 A | 4/1998 | Hoftman |
| 5,746,201 A | 5/1998 | Kidd |
| 5,758,642 A | 6/1998 | Choi |
| 5,813,423 A | 9/1998 | Kirchgeorg |
| 5,832,918 A | 11/1998 | Pantino |
| D402,755 S | 12/1998 | Kwok |
| 5,884,624 A | 3/1999 | Barnett et al. |
| 5,887,587 A | 3/1999 | Groenke |
| 5,896,857 A | 4/1999 | Hely et al. |
| 5,921,239 A | 7/1999 | McCall et al. |
| D412,745 S | 8/1999 | Scheu |
| 5,937,851 A | 8/1999 | Serowski et al. |
| 5,937,855 A | 8/1999 | Zdrojkowski et al. |
| 5,941,245 A | 8/1999 | Hannah et al. |
| 5,954,052 A | 9/1999 | McDonald et al. |
| 5,957,132 A | 9/1999 | McDonald et al. |
| 6,029,660 A | 2/2000 | Calluaud et al. |
| 6,035,852 A | 3/2000 | Hoftman |
| 6,039,044 A | 3/2000 | Sulivan |
| D428,987 S | 8/2000 | Kwok |
| D428,988 S | 8/2000 | Smart |
| 6,112,746 A | 9/2000 | Kwok et al. |
| 6,119,693 A | 9/2000 | Kwok et al. |

| | | | |
|---|---|---|---|
| 6,119,694 A | 9/2000 | Correa et al. | |
| 6,123,071 A | 9/2000 | Berthon-Jones et al. | |
| 6,123,082 A | 9/2000 | Berthon-Jones | |
| D435,650 S | 12/2000 | Kwok | |
| 6,189,532 B1 | 2/2001 | Hely et al. | |
| 6,192,866 B1 | 2/2001 | Araki et al. | |
| 6,192,223 B1 | 3/2001 | Belfer et al. | |
| 6,341,383 B1 | 1/2002 | Beltrani | |
| 6,357,440 B1 | 3/2002 | Hansen et al. | |
| 6,357,441 B1 | 3/2002 | Kwok et al. | |
| 6,374,826 B1 | 4/2002 | Gunaratnam et al. | |
| 6,412,487 B1 | 7/2002 | Gunaratnam et al. | |
| 6,422,238 B1 | 7/2002 | Lithgow | |
| 6,439,230 B1 | 8/2002 | Gunaratnam et al. | |
| 6,463,931 B1 | 10/2002 | Kwok et al. | |
| 6,467,483 B1 | 10/2002 | Kopacko et al. | |
| 6,520,182 B1 | 2/2003 | Gunaratnam | |
| 6,532,961 B1 | 3/2003 | Kwok et al. | |
| 6,550,070 B2 | 4/2003 | Wiegand | |
| 6,679,261 B2 | 1/2004 | Lithgow et al. | |
| 6,691,707 B1 | 2/2004 | Gunaratnam et al. | |
| 6,694,532 B2 | 2/2004 | Chen | |
| 6,701,927 B2 | 3/2004 | Kwok et al. | |
| 6,832,610 B2 | 12/2004 | Gradon et al. | |
| 7,007,696 B2 | 3/2006 | Palkon et al. | |
| 7,207,334 B2 | 4/2007 | Smart | |
| 7,290,546 B2 | 11/2007 | Sprinkle et al. | |
| 2001/0035188 A1 | 11/2001 | Gleason et al. | |
| 2002/0005198 A1 | 1/2002 | Kwok et al. | |
| 2002/0005201 A1 | 1/2002 | Gradon et al. | |
| 2002/0014241 A1 | 2/2002 | Gradon et al. | |
| 2002/0023649 A1 | 2/2002 | Gunaratnam et al. | |
| 2002/0023650 A1 | 2/2002 | Gunaratnam et al. | |
| 2002/0026934 A1 | 3/2002 | Lithgow et al. | |
| 2002/0029780 A1 | 3/2002 | Frater et al. | |
| 2002/0029781 A1 | 3/2002 | Kwok et al. | |
| 2002/0083948 A1 | 7/2002 | Kwok et al. | |
| 2002/0100479 A1 | 8/2002 | Scarberry et al. | |
| 2002/0104540 A1 | 8/2002 | Kwok et al. | |
| 2002/0108613 A1 | 8/2002 | Gunaratnam et al. | |
| 2002/0134388 A1 | 9/2002 | Chang | |
| 2002/0148473 A1 | 10/2002 | Kwok et al. | |
| 2002/0157672 A1 | 10/2002 | Gunaratnam et al. | |
| 2002/0185134 A1 | 12/2002 | Bishop | |
| 2003/0019495 A1 | 1/2003 | Palkon et al. | |
| 2003/0075180 A1 | 4/2003 | Raje et al. | |
| 2004/0004551 A1 | 1/2004 | Eaton et al. | |
| 2004/0255949 A1 | 12/2004 | Lang et al. | |

FOREIGN PATENT DOCUMENTS

| | | |
|---|---|---|
| AU | 41018/97 | 4/1998 |
| AU | 89312/98 | 1/1999 |
| AU | 712236 | 11/1999 |
| AU | 724360 | 9/2000 |
| AU | 728849 | 1/2001 |
| CA | 1039144 | 9/1978 |
| CA | 2261790 | 2/1998 |
| CA | 2295457 | 7/2000 |
| CA | 2298129 | 8/2000 |
| DE | 3345067 | 5/1985 |
| DE | 3537507 | 4/1987 |
| DE | 3539073 | 5/1987 |
| DE | 4004157 | 4/1991 |
| DE | 4343205 | 6/1995 |
| DE | 19735359 | 1/1998 |
| DE | 3707952 | 9/1998 |
| DE | 29810846 | 12/1999 |
| DE | 19962515 | 7/2001 |
| EP | 54154 | 10/1981 |
| EP | 178925 | 10/1985 |
| EP | 252052 | 7/1987 |
| EP | 264772 | 10/1987 |
| EP | 386605 | 2/1990 |
| EP | 427474 | 11/1990 |
| EP | 462701 | 5/1991 |
| EP | 602424 | 11/1993 |
| EP | 608684 | 1/1994 |
| EP | 697225 | 7/1995 |
| EP | 747078 | 6/1996 |
| EP | 821978 | 7/1997 |
| EP | 958841 | 11/1999 |
| EP | 1027905 | 8/2000 |
| EP | 1266674 | 12/2002 |
| FR | 1100270 | 5/1954 |
| FR | 2574657 | 6/1986 |
| FR | 2658725 | 8/1991 |
| FR | 2749176 | 12/1997 |
| GB | 697762 | 9/1953 |
| GB | 848215 | 9/1960 |
| GB | 1395391 | 5/1975 |
| GB | 1467828 | 3/1977 |
| GB | 2145335 | 3/1985 |
| GB | 2164569 | 3/1986 |
| GB | 2147506 | 4/1987 |
| GB | 2267648 | 7/1996 |
| JP | 9216240 | 8/1997 |
| WO | WO 80/01044 | 5/1980 |
| WO | WO 82/03548 | 10/1982 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 96/17643 | 6/1996 |
| WO | WO 96/25983 | 8/1996 |
| WO | WO 96/39206 | 12/1996 |
| WO | WO 97/07847 | 3/1997 |
| WO | WO 97/41911 | 11/1997 |
| WO | WO 98/04310 | 2/1998 |
| WO | WO 98/11930 | 3/1998 |
| WO | WO 98/18514 | 5/1998 |
| WO | WO 98/24499 | 6/1998 |
| WO | WO 98/26829 | 6/1998 |
| WO | WO 98/26830 | 6/1998 |
| WO | WO 98/34665 | 8/1998 |
| WO | WO 98/48878 | 11/1998 |
| WO | WO 00/57942 | 10/2000 |
| WO | WO 00/78381 | 12/2000 |
| WO | WO 00/78382 | 12/2000 |
| WO | WO 00/78383 | 12/2000 |
| WO | WO 00/78384 | 12/2000 |
| WO | WO 02/45784 | 6/2002 |
| WO | WO 03/082406 | 10/2003 |
| WO | 2005/123166 | 12/2005 |
| WO | 2006/074517 | 7/2006 |

OTHER PUBLICATIONS

Communication from EP 03745562.3, 6 pgs., mailed Jul. 12, 2007.
ResMed Ltd., Mirage Activa Nasal Mask, Components Card, one page brochure, 2005.
ResMed Ltd., Mirage Activa Mask, User's Guide, 12 pgs., 2003.
ResMed Ltd., Ultra Mirage Full Face Mask, User Guide, 67 pgs., 2005.
ResMed Ltd., Ultra Mirage II Nasal Mask, User Guide, 52 pgs., 2005.
Sunrise Medical, FlexAire, Devilbiss, Dare to Dream, 2 pg. brochure, copyright Aug. 2003.
Sunrise Medical, Flexset, DeVilbiss, 2 pg. brochure, copyright 2005.
Sunrise Medical, Sleep Therapy, Devilbiss, 10 pg. brochure, copyright Aug. 2006.
Sunrise Medical, DeVilbiss, DeVilbiss FlexAire Mask, 9353 Series Instruction Guide, 52 pgs., copyright Feb. 2004.
Invacare Corporation, Invacare Sleepy Therapy Products, 4 pg. brochure, copyright 2005.
Invacare Corporation, Sleepy Therapy, Twilight II Mask, 2 pg. brochure, copyright 2006.
Invacare Corporation, Invacare Twilight Nasal Mask and Headgear, Model No. ISP2000 Standard, 12 pgs., copyright 2003.
Invacare Corporation, Invacare Twilight II Nasal Mask, Assembly, Installation and Operating Instructions, 20 pgs., copyright 2006.
Communication from European Application No. 07116625.0 dated Jun. 9, 2010.

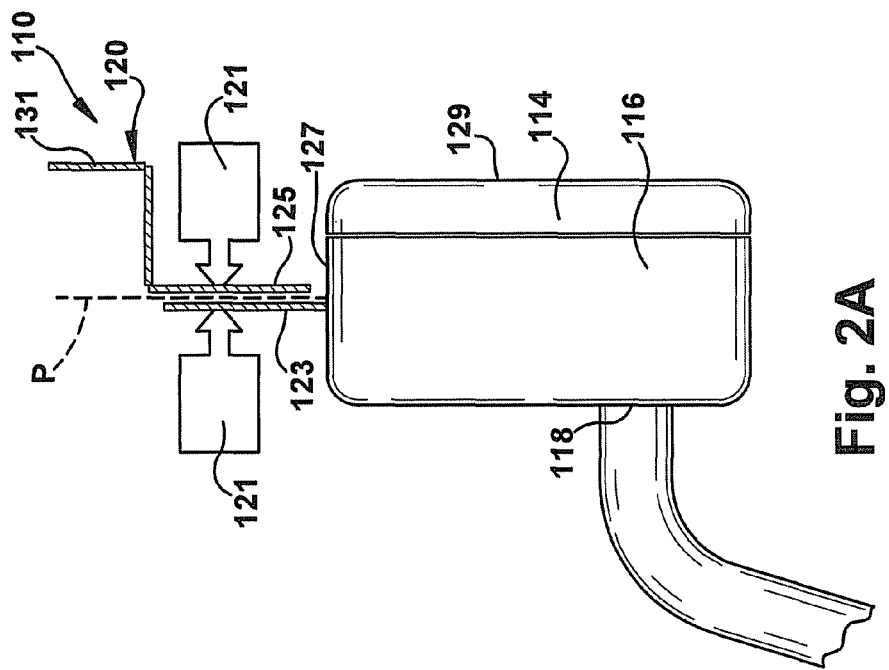
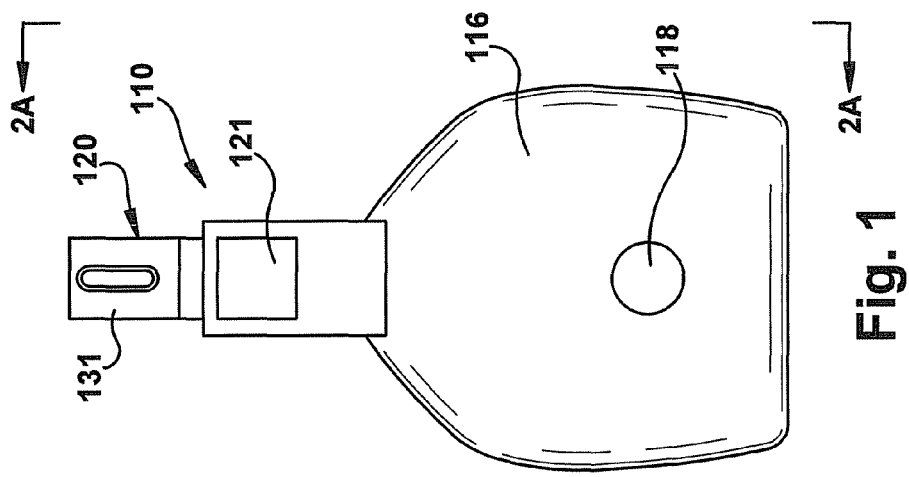

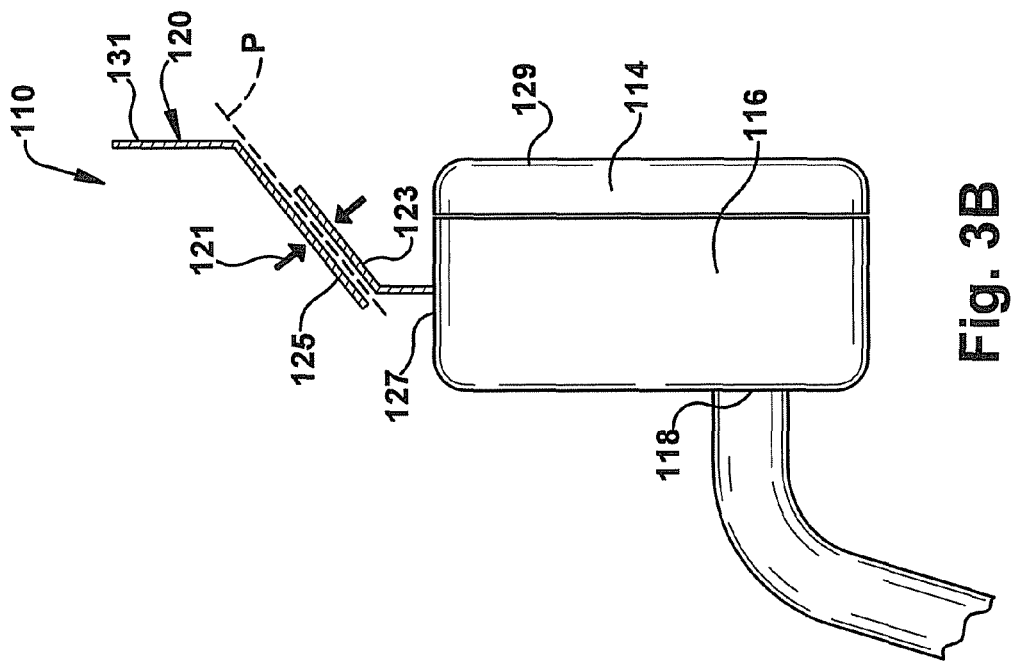
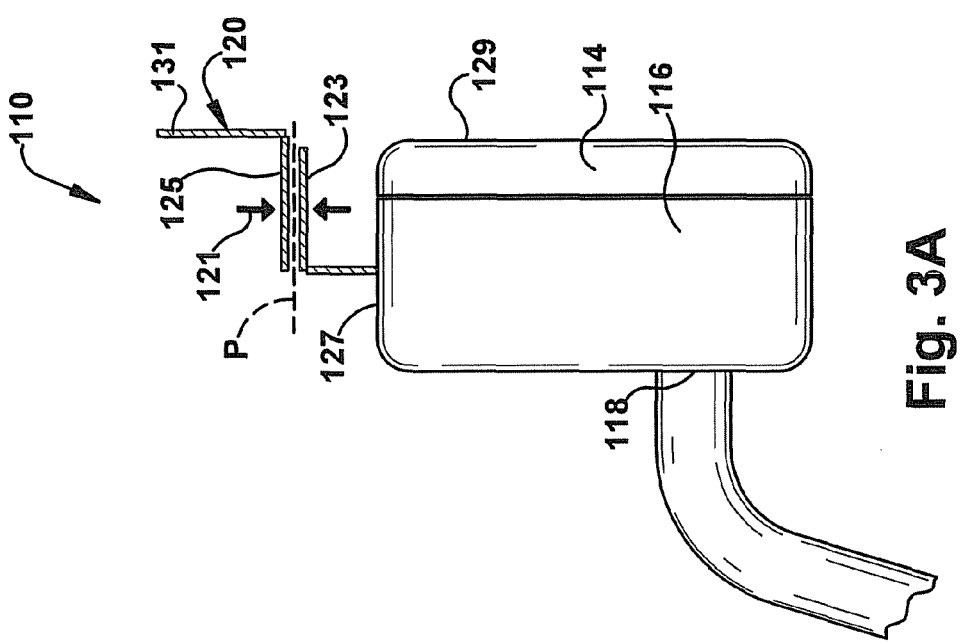

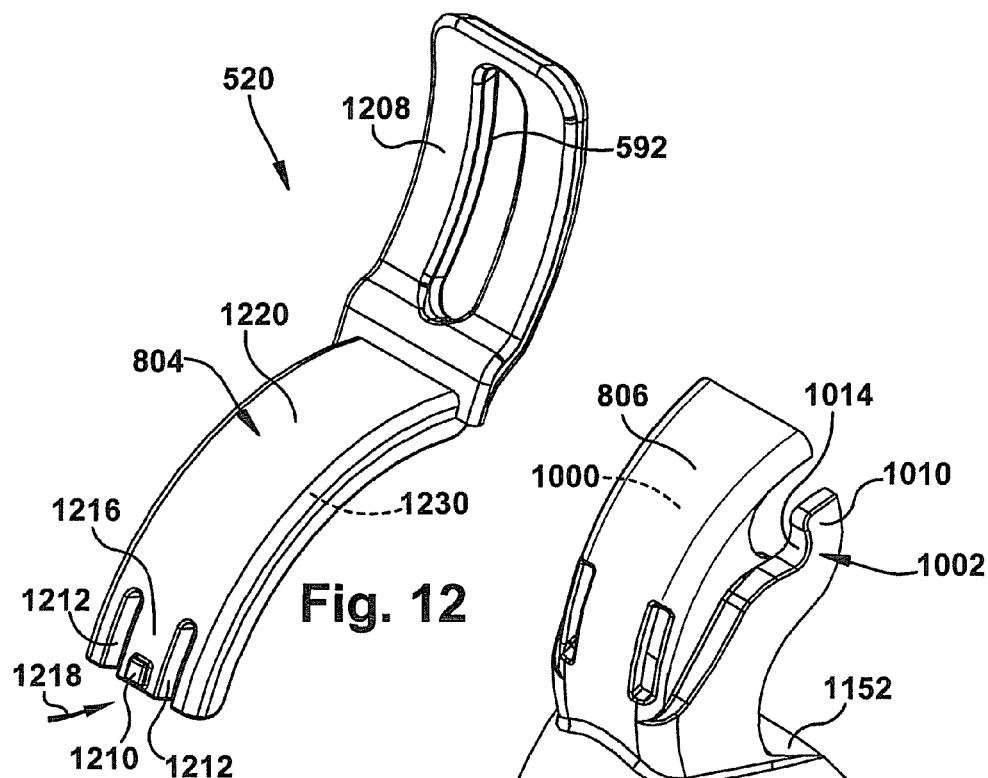
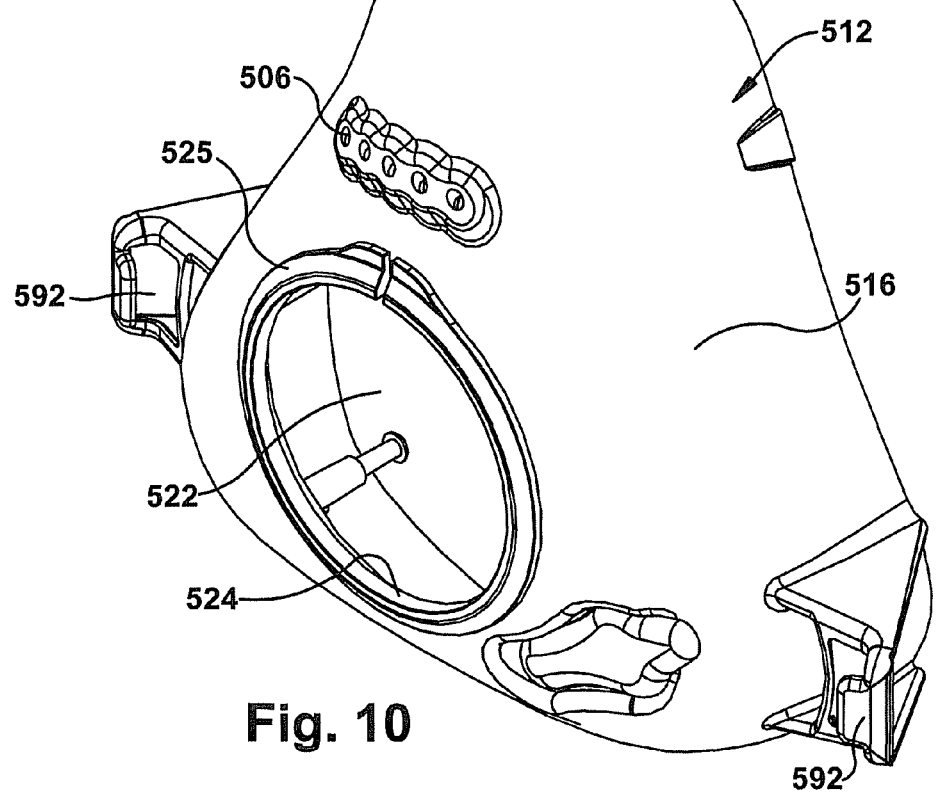

BREATHING MASK

RELATED APPLICATIONS

The present application claims the benefit of provisional patent application Ser. No. 60/826,015 filed on Sep. 18, 2006, entitled "Breathing Mask." Provisional patent application Ser. No. 60/826,015 is incorporated herein by reference in its entirety.

BACKGROUND

Breathing masks may be used to deliver gases of controlled composition, at a controlled pressure, and at a controlled flow to a person's face for inhalation. Gas composition typically is controlled to achieve a particular medical goal, such as anesthesiology. Gas pressure typically is controlled to ease or assist the breathing process, made difficult for example due to high altitude or a medical condition afflicting the user.

The breathing masks are used to apply continuous positive airway pressure ("CPAP") treatment for sleep disorders, such as obstructive sleep apnea. Pursuant to this treatment the user wears a breathing mask while sleeping. A device delivers air to the breathing mask at a pressure above atmospheric pressure. This helps the user to breath more normally during sleep. Further descriptions of CPAP treatments and devices can be found in U.S. Pat. Nos. 5,199,424 and 5,433,193, which are hereby fully incorporated by reference.

SUMMARY

Embodiments of breathing mask assemblies that include adjustable forehead support are disclosed herein. In one embodiment, a forehead support is adjustably coupled to a central body of the breathing mask. A clamp is configured to lock the position of the forehead support relative to the central body and to lock the forehead support at multiple different positions. In one exemplary embodiment, the forehead support may be locked at any position along a path of travel between a first position and a second position.

DESCRIPTION OF THE FIGURES

FIG. 1 is a schematic illustration of a breathing mask that includes a forehead support coupled to a mask central body;

FIG. 2A is a view taken along lines 2A-2A in FIG. 1;

FIG. 3A is a view similar to FIG. 2A showing another embodiment of a coupling between the forehead support and the mask central body;

FIG. 3B is a view similar to FIG. 2A showing another embodiment of a coupling between the forehead support and the mask central body;

FIG. 10 is a perspective view of a central body of a breathing mask assembly;

FIG. 12 is a perspective view of a forehead support;

WRITTEN DESCRIPTION OF PREFERRED EMBODIMENTS

Figure 2B:
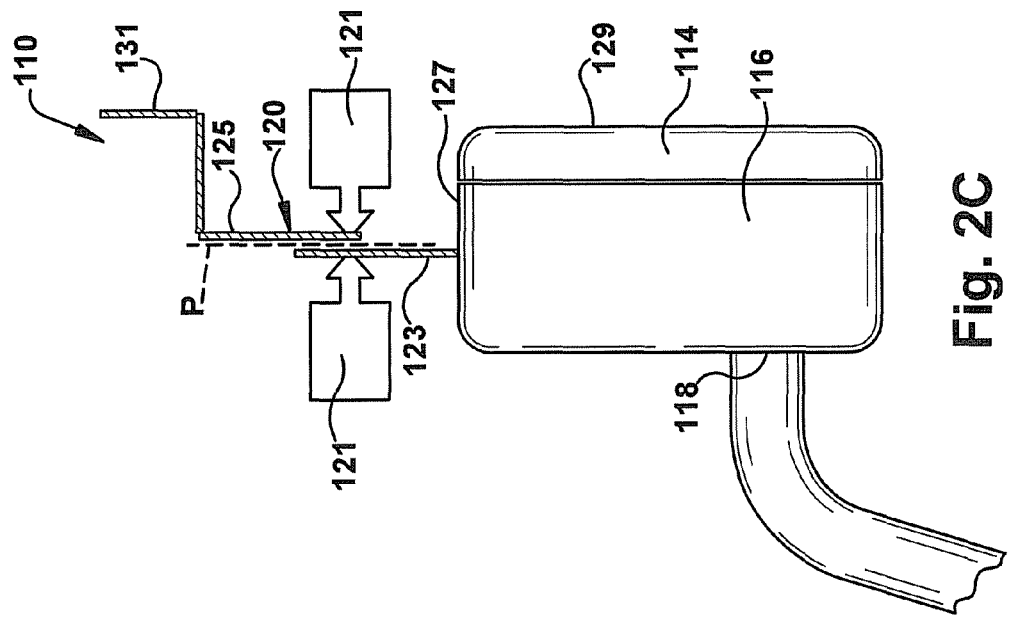
FIG. 2B is a view similar to FIG. 2A with a forehead support moved outward relative to the mask.

Referring to the Figures, the present application discloses embodiments of breathing mask assemblies that each include an adjustable forehead support. Breathing masks may take a variety of different forms. Examples of breathing masks include, but are not limited to, nasal masks, which cover a user's nose, nasal/oral masks, which cover a user's mouth and nose, and oral masks, which cover a user's mouth. A variety of different features are included in the different breathing mask assembly embodiments that are disclosed in this application. The scope of this application is intended to encompass all combinations and sub-combinations of the features of the breathing mask assembly embodiments disclosed in this application.

Referring to FIGS. 1 and 2A, one embodiment of a breathing mask assembly 110 includes a central body 116 that includes an inlet aperture 118 for receiving a delivered gas and is configured to deliver the gas to a nose and/or a mouth of the user. The central body 116 may be adapted to deliver the gas to the nose and/or mouth of a user in a wide variety of different ways. For example, the central body 116 and an optional face cushion 114 may be sized and shaped to fit over a user's mouth and nose, may be sized and shaped to fit over a user's mouth only, or may be sized and shaped to fit only over the user's nose.

In this application, the term "forehead support" encompasses any component of a breathing mask assembly that is configured to rest on a user's forehead and support a portion of the weight of the breathing mask assembly. Forehead supports may take a wide variety of configurations and are not limited to the configurations illustrated herein.

In one embodiment, a forehead support 120 is adjustably coupled to the central body 116. The forehead support assembly may be adjustably coupled to the central body 116 in a wide variety of different ways. Examples of couplings between the central body 116 and the forehead support 120 include, but not limited to, pivotal connections, slideable connections, or any other connection that allows the forehead support 120 to move along a path of travel with respect to the central body 116. The forehead support 120 may be coupled to the central body 116 such that the forehead support 120 is movable along a path of travel from a first position to a second position. In one exemplary embodiment, the breathing mask assembly 110 includes a clamp 121 arranged to secure the forehead support 120 with respect to the central body 116 at any position between the first and second positions. That is, the clamp 121 can couple the forehead support 120 at an unlimited number of locations between the first and second positions. The clamp 121 can take a wide variety of different forms. Examples of acceptable clamps 121 include, but are not limited to, threaded clamping arrangements, wedge-type clamping arrangements, and cam-type clamping arrangements. Any arrangement that selectively fixes the position of the forehead support 120 with respect to the central body 116 may be used.

Figure 2C:
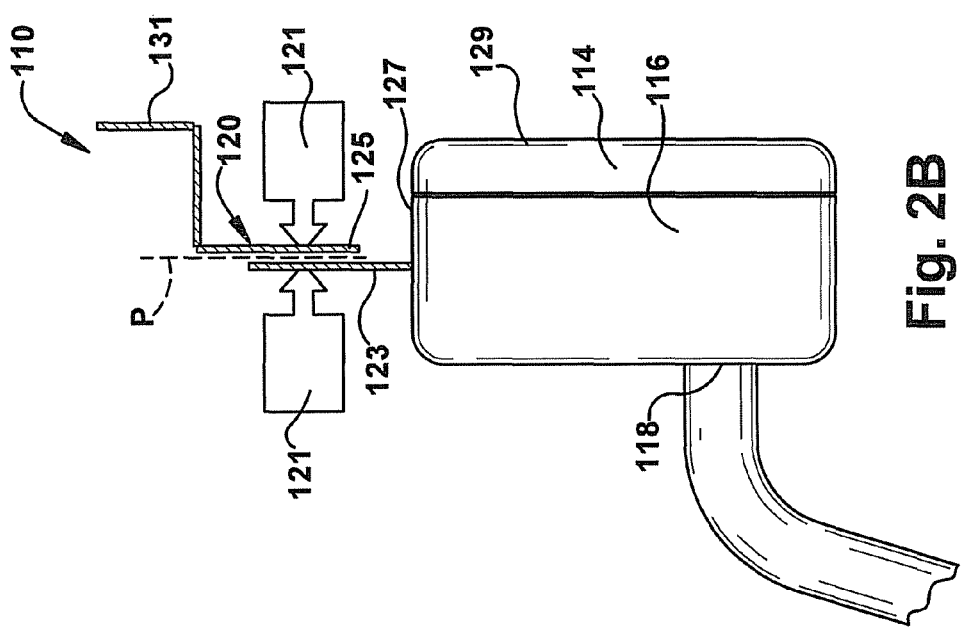
FIG. 2C is a view similar to FIG. 2B with the forehead support moved further outward relative to the mask.

The FIGS. 1 and 2A breathing mask assembly 110 embodiment includes an adjustable forehead support 120, a central body 116, a central body slide surface 123, a forehead support slide surface 125, and a clamp 121. The central body slide surface 123 is coupled to the central body 116. The central body slide surface 123 may be coupled to the central body 116 in a wide variety of different ways. For example, the central body slide surface 123 may be adjustably coupled to the central body 116, may be fixed to the central body, or may be formed integrally with the central body. The forehead support surface 125 is coupled to the forehead support 120. The forehead support slide surface 125 may be coupled to the forehead support 120 in a wide variety of different ways. For example, the forehead support slide surface 125 may be adjustably coupled to the forehead support 120, may be fixed to the forehead support, or may be formed integrally with the forehead support. The forehead support slide surface 125 is slideably coupled to the central body slide surface 123 such that the forehead support 120 is moveable along a path of travel P defined by the slide surfaces 123, 125. The forehead support 120 is moveable from a first position (see for example FIG. 2A) to a second position (see for example FIG. 2C) along the path of travel P. The first and second positions may correspond to any two positions along the path of travel P. FIG. 2A shows a fully retracted position, FIG. 2B shows an intermediate position, and FIG. 2C shows a fully extended position. The clamp 121 is coupled to the central body slide surface 123 and the forehead support slide surface 125. The clamp is configured to lock the position of the forehead support slide surface 125 relative to the central body slide surface 123 at any position along the path of travel P. This allows the position of the forehead support 120 to be locked at the fully retracted position (FIG. 2A), and the fully extended position (FIG. 2C), or any position in between (see for example FIG. 2B).

Figure 3C:
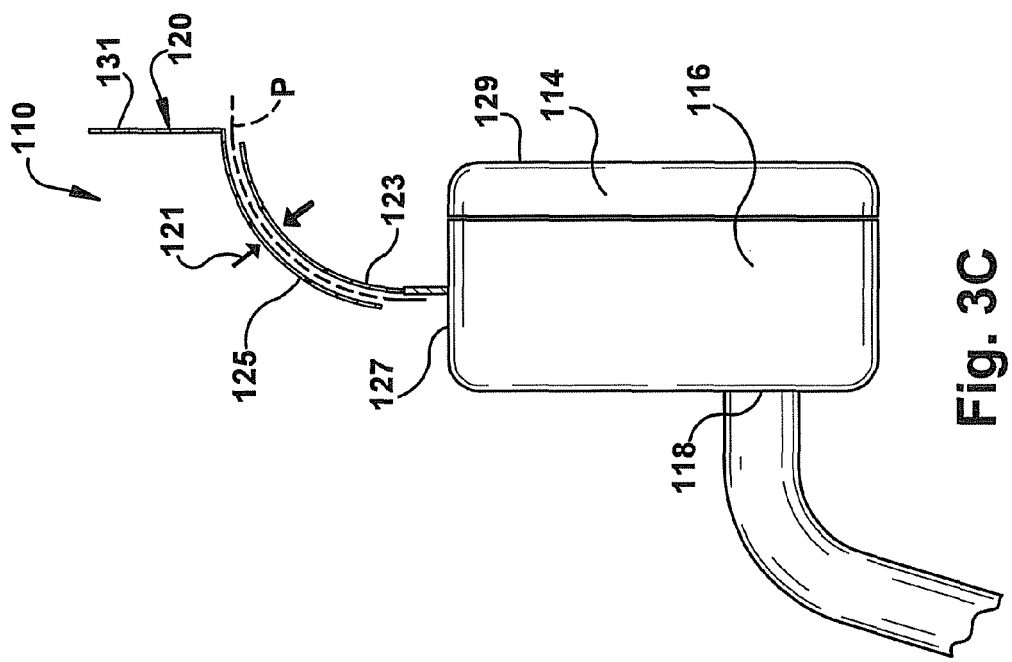
FIG. 3C is a view similar to FIG. 2A showing another embodiment of a coupling between the forehead support and the mask central body.

The slide surfaces 123, 125 may be configured to define a wide variety of different paths of travel P. In the example illustrated by FIGS. 2A-2C, the path of travel P is linear and extends generally orthogonally away from an end surface 127 of the central body 116. In the example illustrated by FIG. 3A, the path of travel is linear and extends generally orthogonally away from a face engaging surface 129. In the example illustrated by FIG. 3B, the path of travel P is linear and extends away from the end surface 127 at an angle. In the example illustrated by FIG. 3C, the path of travel P is curved. A curved path of travel adjusts both the position and an angular orientation of a portion 131 of the forehead support 120 that is supported by a users forehead. By adjusting the angular orientation of the portion 131, variations in the slopes of foreheads are accommodated for a more comfortable fit.

Figure 4:
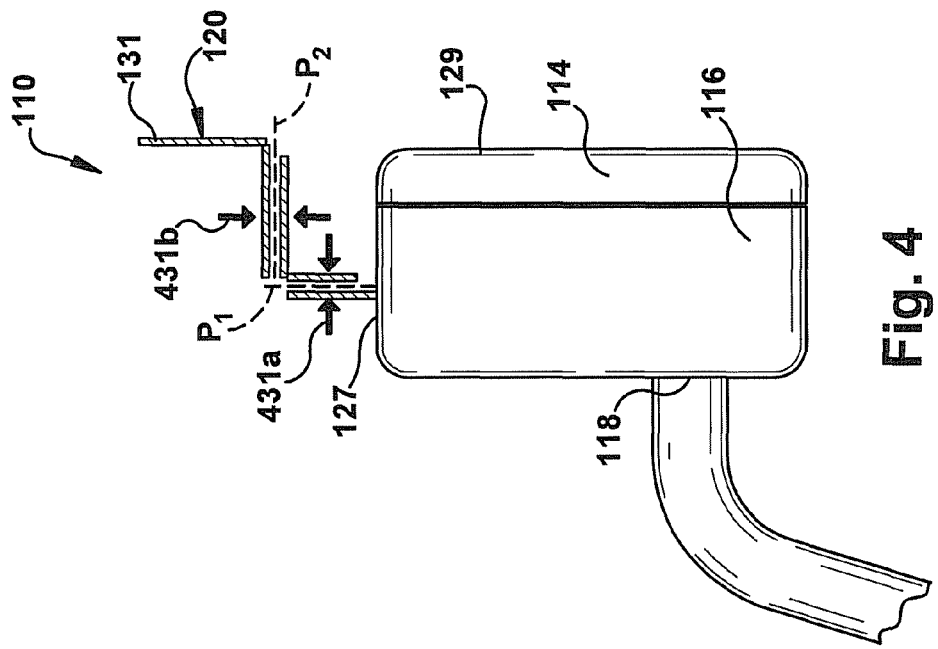
FIG. 4 is a view similar to FIG. 2A showing another embodiment of a coupling between the forehead support and the mask central body.

FIG. 4 illustrates an embodiment where two clamps 431a, 431b are included to provide two degrees of freedom of the forehead support 120 with respect to the central body 116. Each clamp 431a, 431b allows the forehead support 120 to move along a different path of travel P1, P2. This allows forehead support 120 to be moved in two directions with respect to the central body 116. In the example illustrated by FIG. 4, the first path of travel P1 extends orthogonally away from the end surface 127 of the central body 116 and the second path of travel extends generally orthogonally away from a face engaging surface 129. However, any two paths of travel may be defined. For example, two curved paths of travel may be defined by slideable surfaces, one straight path of travel and one curved path of travel may be defined by slideable surfaces, one straight path of travel may be defined by a slideable surface and a path of travel may be defined by a pivotal connection, or one curved path of travel may be defined by a slideable surface and a path of travel may be defined by a pivotal connection. Additional paths of travel may be defined to provide additional degrees of freedom of the forehead support 120 with respect to the central body 116.

An adjustable forehead support 120 may be included in a wide variety of different breathing mask assemblies. One such breathing mask assembly is disclosed in Patent Application Publication Pub. No. US2005/0011521, published on Jan. 20, 2005, which is incorporated herein by reference in its entirety.

Figure 5:
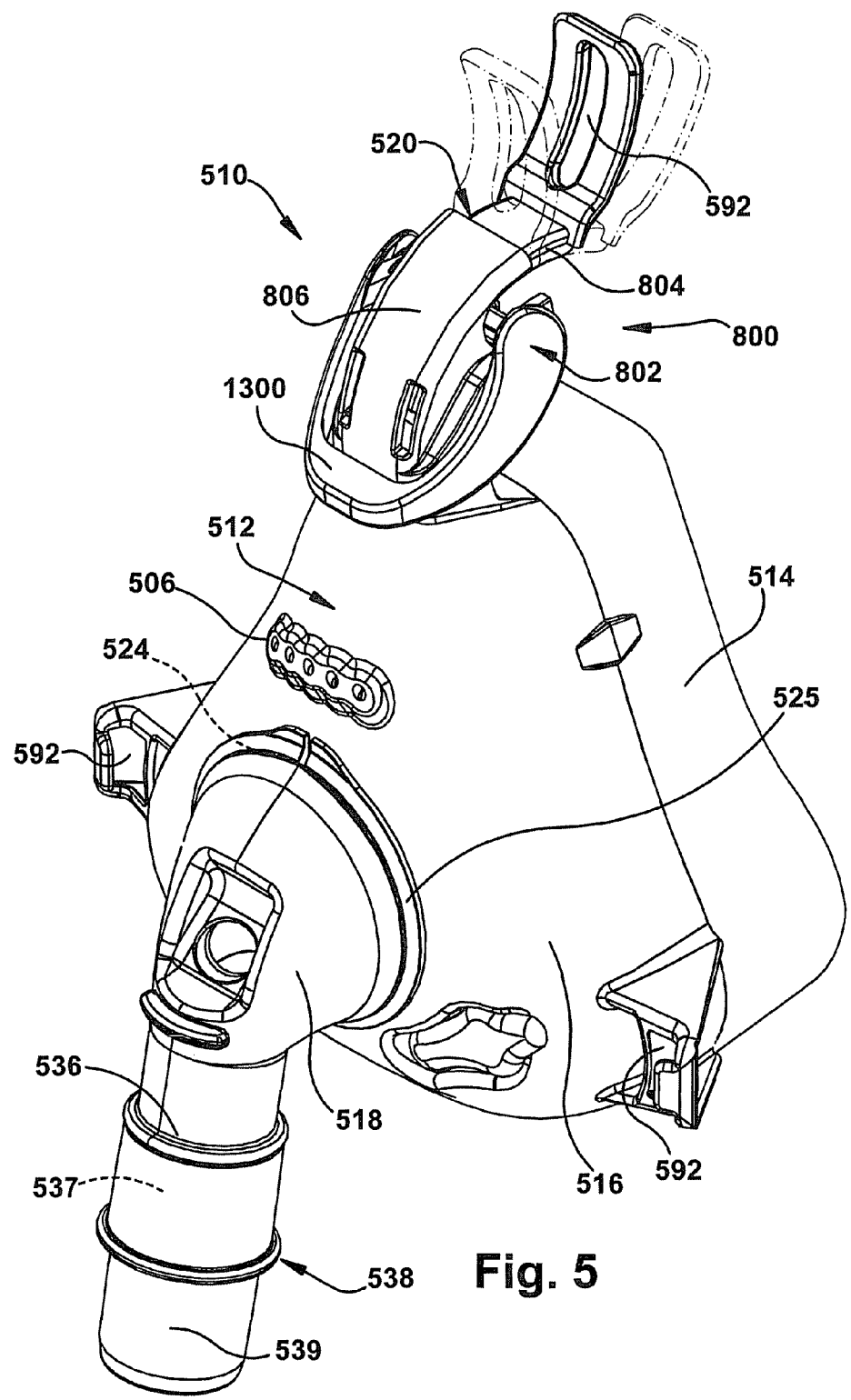
FIG. 5 is a perspective view of an embodiment of a breathing mask assembly.
Figure 6:
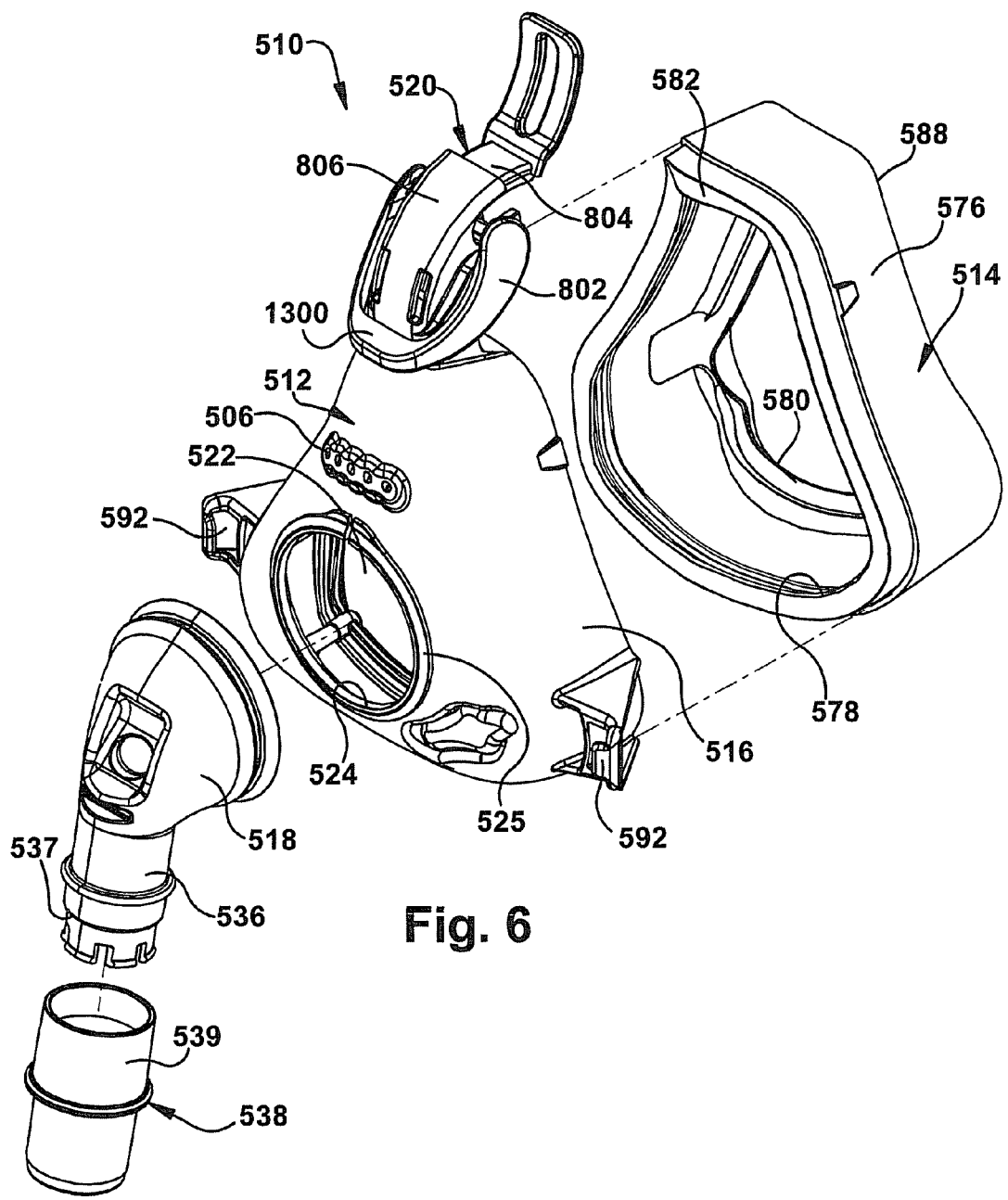
FIG. 6 is an exploded perspective view of the breathing mask assembly shown in FIG. 5.
Figure 7:
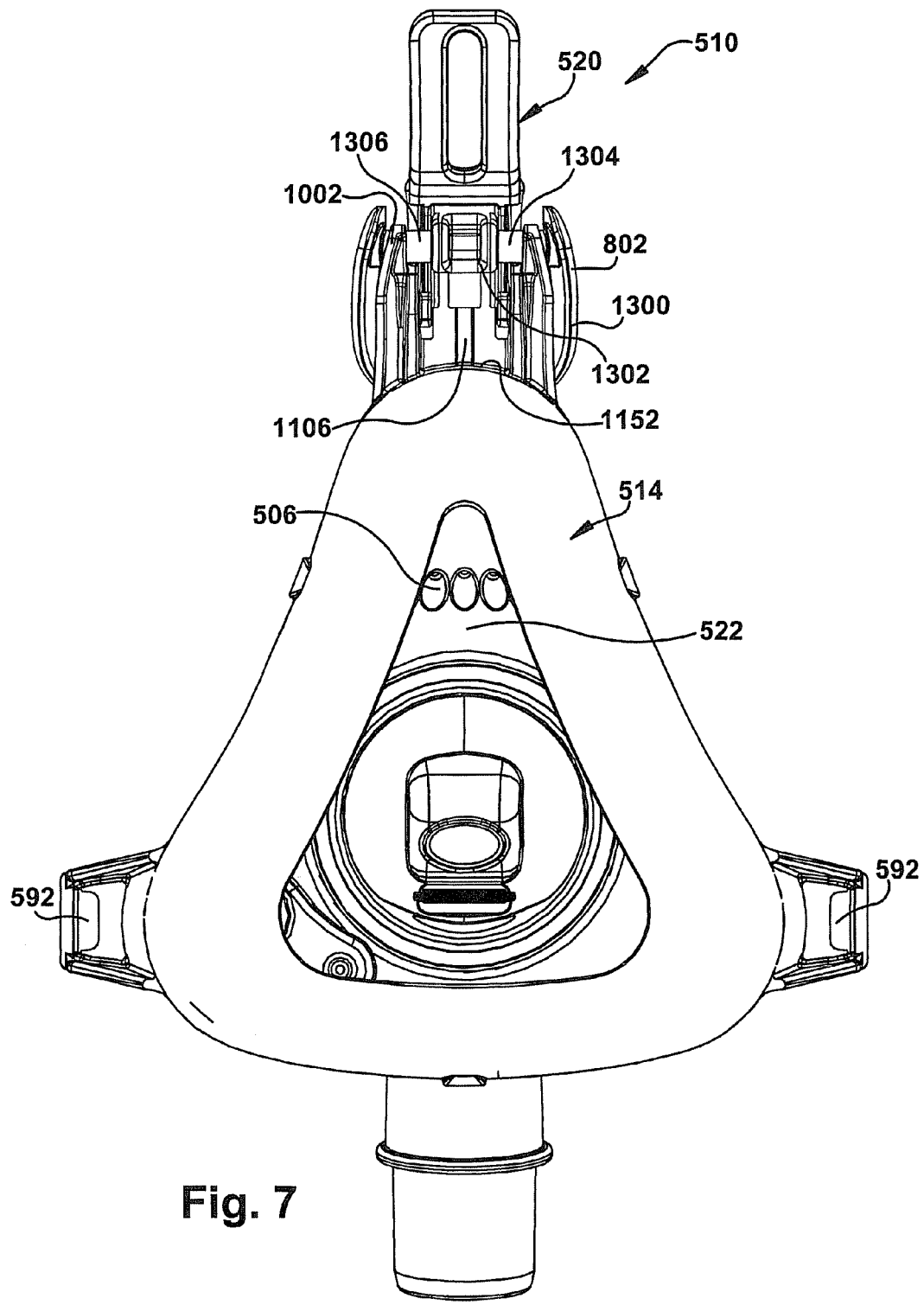
FIG. 7 is a rear view of the breathing mask assembly shown in FIG. 5.

FIGS. 5-7 illustrate an embodiment of a breathing mask assembly 510 with an adjustable forehead support 520. In the example illustrated by FIGS. 5-7, the breathing mask assembly is configured to cover the user's mouth and nose. The breathing mask assembly 510 has two main components, a shell 512 and a face cushion 514. The shell 512 is preferably made of plastic, which may be optically transparent. The plastic should be impermeable to gas or air. The shell 512 has several parts, including a central body 516, a gas inlet 518 and a forehead support 520.

Referring to FIGS. 6 and 7, the central body 516 defines a central cavity 522. A circular inlet aperture 524 in the front of the central body 516 permits air to enter the central cavity 522. The gas inlet 518 is rotatably attached to the central body 516 so that it covers the circular aperture 524. The gas inlet 518 can be connected to the circular aperture 524 in a wide variety of different ways. Referring to FIGS. 5 and 6, in one embodiment, the gas inlet 518 is connected to the circular aperture 524 by a circular clip 525. Any attachment arrangement may be used and the gas inlet may or may not be able to rotate with respect to the central body once attached.

The gas inlet 518 extends to a cylindrical tube portion 536. The cylindrical tube portion 536 connects to a flexible gas delivery tube (not shown in the drawings) in such a way that the tube may rotate with respect to the cylindrical tube portion 536. A wide variety of suitable rotatable connections may be used. FIGS. 5 and 6 illustrate one example of a fitting 538 that permits rotation for connecting a tube of a CPAP machine to the tube portion 536. The rotation fitting 538 has two cylindrical portions 537, 539 that are relatively rotatable. The first cylindrical portion 537 is formed as part of the gas inlet 518. The second cylindrical portion 539 is a separate member that is rotatably connected to the first member.

Referring to FIG. 6, the face cushion 514 serves two basic functions: user comfort and sealing. Thus the face cushion 514 should be made of a bio-friendly elastomeric material which is both substantially gas impermeable and elastic enough to conform comfortably to the contours of a person's face. One acceptable material for the face cushion is silicone. The face cushion 514 may take any shape. The illustrated face cushion 514 comprises a cushion body 576 having two opposed openings, a mask-side or "front" opening 578 and a face-side or "rear" opening 580. A front rim 582 defining the front opening 578 sealingly fits into the rear of the shell's central body 516.

The cushion body 576 extends from the front rim 582 to a rear rim 588. The cushion body 576 is sufficiently thick that its elastomeric properties can provide a cushioning effect between the breathing mask 510 and the user's face when the mask 510 is worn, but not so long to make the mask 510 cumbersome to use during sleep. The cushion body 576 is sufficiently thick to provide cushioning and to prevent deformation due to pressure on the breathing mask 510 when tightened down on to the user's head.

For the most efficient operation, the breathing mask assembly 510 should be held against the user's face. This ensures a sufficiently tight seal so that an elevated pressure is maintained within the mask assembly 510 and the gas delivered to the mask assembly does not leak to the outside environment. The breathing mask assembly 510 may include securing structures 592 for attaching straps (not shown) to the mask 510. The securing structures 592 may take a wide variety of different forms. Examples of acceptable securing structures 592 include, but are not limited to slots and structures that allow a clip to be attached to the mask. The securing structure 592 may be any structure that allows straps to be attached to the mask assembly. If the securing structure is a slot, a strap end may be looped through the slot and then secured, preferably with a snap or hook and loop connection. Regardless of how the strap is attached to the mask, once attached, the strap then may be wrapped around the user's head and adjusted to provide a tight enough fit for maintaining a proper seal, but loose enough for the comfort of the user. The securing structures 592 are preferably located on opposite sides of the central body 516, and on the forehead support 520. The securing structures 592 may be positioned at a wide variety of different locations on the mask assembly to comfortably secure the mask to the user's head.

The breathing mask 510 illustrated by FIGS. 5-7 may be used in the following manner. First the user puts the mask 510 on his or her head and adjusts the head straps to achieve a comfortable but sealingly tight fit. A machine operates to supply air of a desired composition and pressure to a tube (not shown), as known in the art. The supplied air travels through the tube and into the tube portion 536 of the mask 510. From there the air travels into the mask shell's central cavity 522, through the face cushion's front and rear openings 578, 580 and into the user's mouth and nose, to be inhaled by the user.

The breathing mask 510 illustrated by FIGS. 5-7 may incorporate one or more exhaust ports 506 to permit gas exhaled by the user (e.g. carbon dioxide) to exit the mask 510 before the user's next inhalation. The exhaust port(s) 506 may be located somewhere in the face cushion 514, in the central body 516, in the gas inlet 518, or even in the tube somewhere proximate the breathing mask 510. In the drawings the exhaust ports 506 are shown in the central body 516. Any exhaust port design which permit exhaust of gas exhaled by the user may be used.

The mask illustrated by FIGS. 5-7 is a nasal/oral mask that is sized to fit over the user's mouth and nose. In one embodiment, the mask illustrated by FIGS. 5-7 is modified to form a nasal mask by sizing the central body 516 and face cushion 514 to fit the user's nose only. In another embodiment, two separate nasal and mouth bodies are connected by an airway conduit. In another embodiment, the mask 510 is modified to form a mouth only mask.

Figure 8:
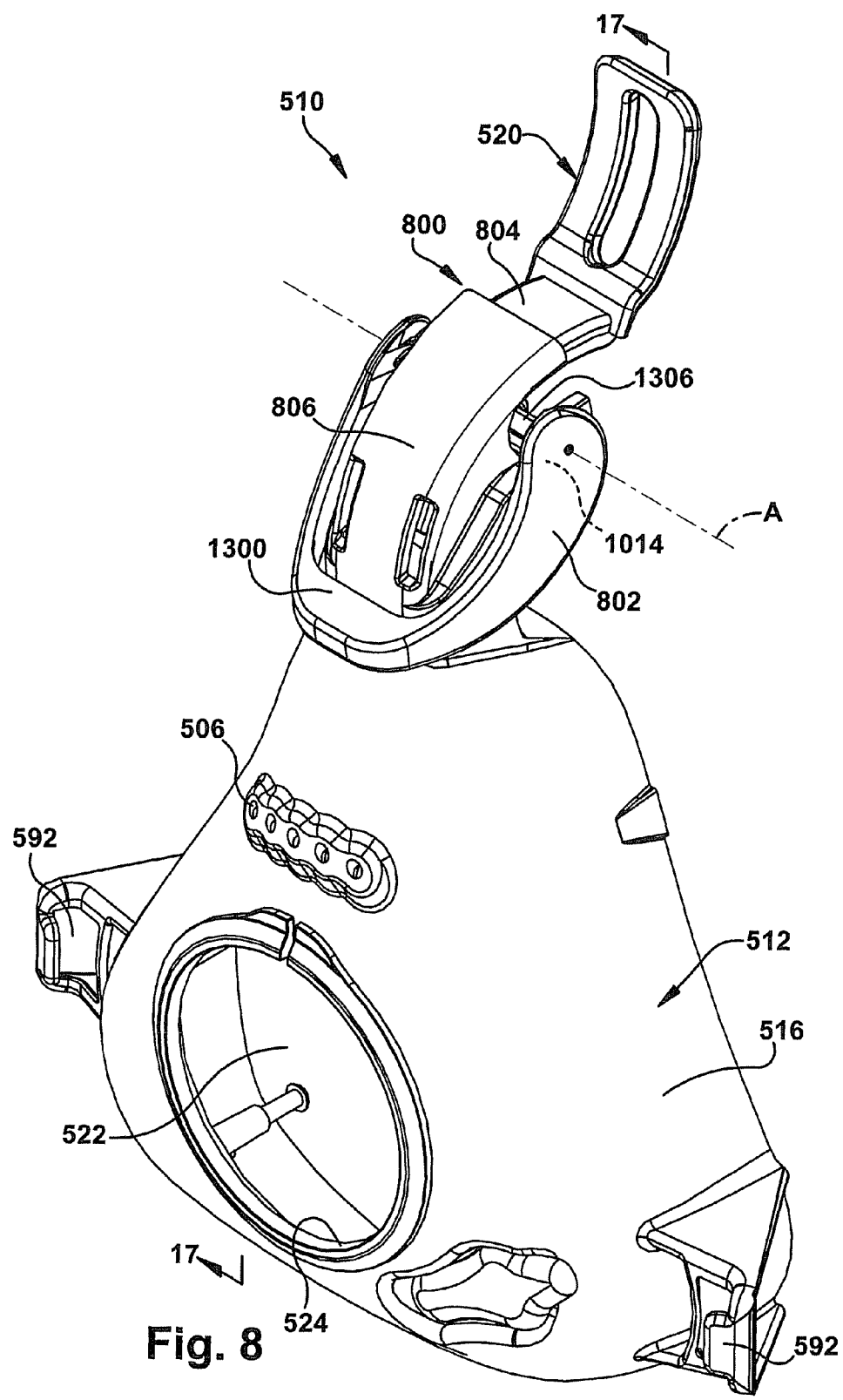
FIG. 8 is a perspective view similar to FIG. 5 with components of the mask assembly removed to more clearly illustrate a forehead support coupling arrangement.
Figure 9:
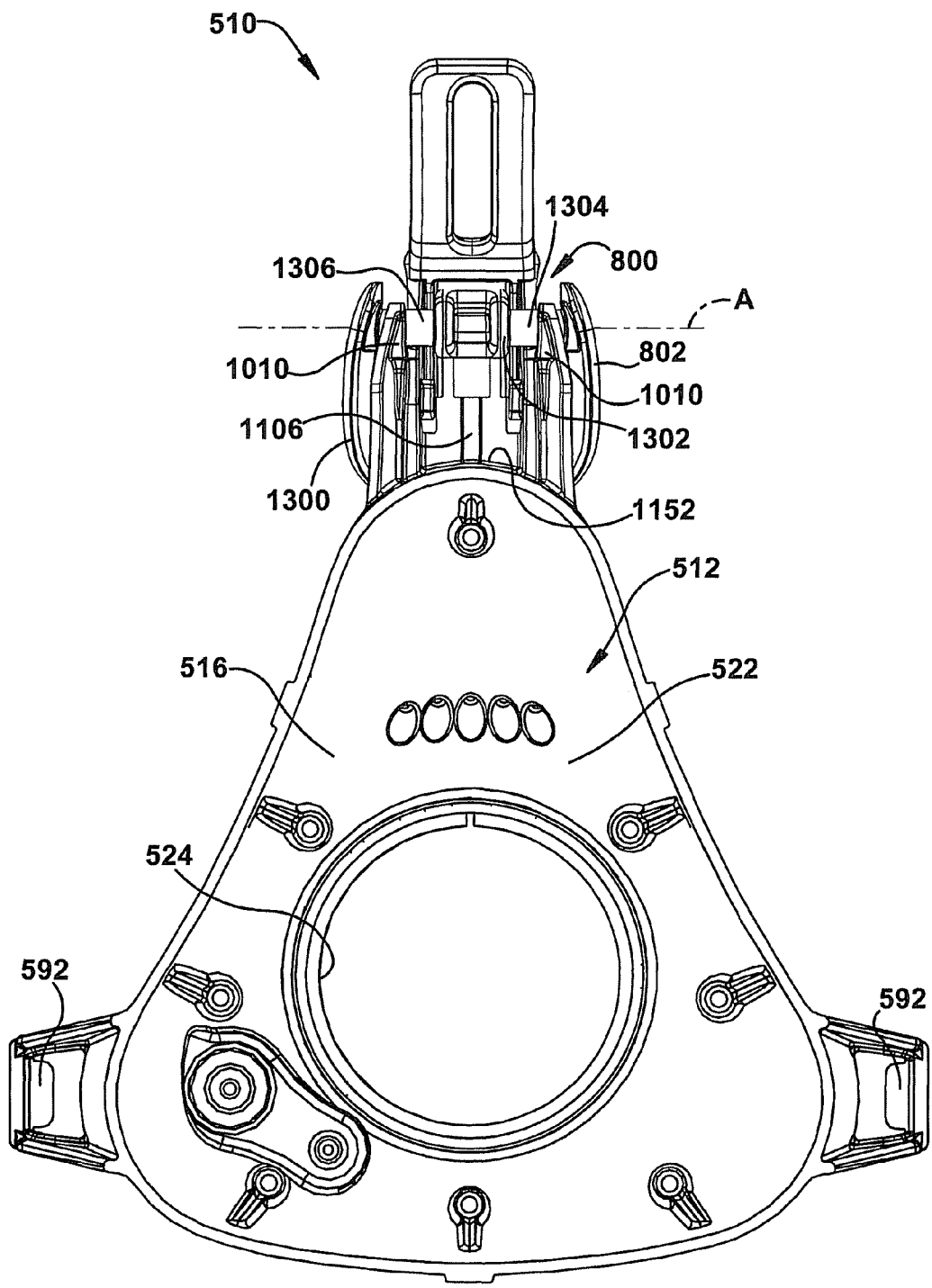
FIG. 9 is a rear view of the breathing mask assembly components shown in FIG. 8.

FIGS. 8 and 9 show the mask assembly 510 illustrated by FIGS. 5-7 with components removed to more clearly illustrate a coupling arrangement 800 that adjustably couples the forehead support 520 to the central body 516. The coupling arrangement 800 comprises a cam member 802, a forehead support slide portion 804, and a central body slide portion 806.

Figure 11:
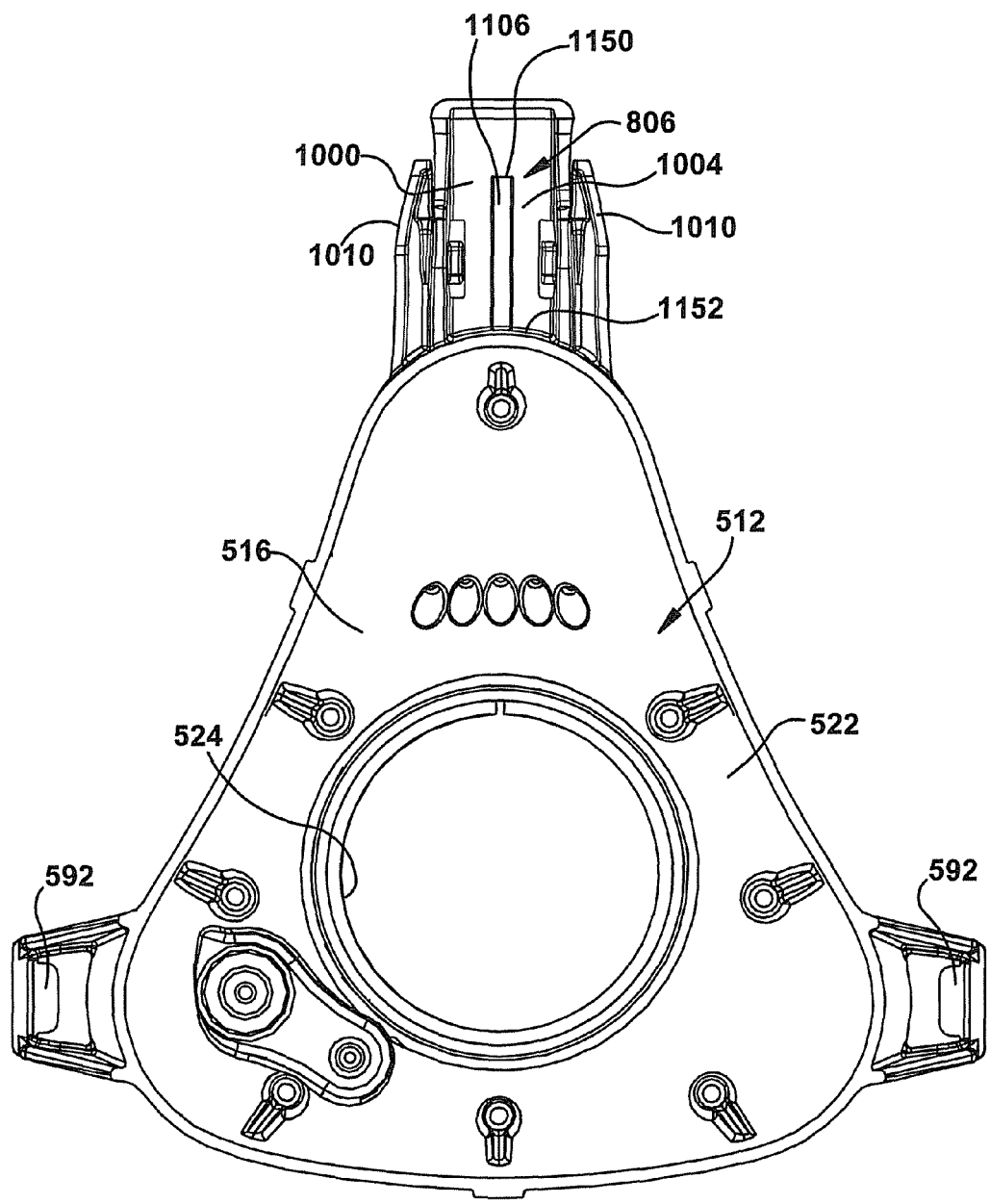
FIG. 11 is a rear view of the breathing mask central body shown in FIG. 10.

Referring to FIGS. 10 and 11, the central body slide portion 806 is integrally formed with the central body 516. The central body slide portion 806 defines a central body slide chamber 1000 (see FIGS. 11 and 16B) and a cam member mount 1002 (see FIGS. 10 and 16B). The slide chamber 1000 has an inner surface 1004 (see FIG. 16A) with a profile that corresponds to the path of travel of the forehead support 520 with respect to the central body 516. Referring to FIG. 11, a stop slot 1106 is defined in the slide chamber 1000. Referring to FIGS. 10 and 11, the cam member mount 1002 comprises arms 1010, disposed on opposite sides of the slide chamber 1000. Each arm includes an arcuate notch 1014.

Referring to FIG. 12, the forehead support 520 includes a forehead supported portion 1208, and the forehead support slide portion 804. The forehead supported portion 1208 is sized and shaped to be supported by a user's forehead to support a portion of the mask assembly's weight. The forehead supported portion 1208 includes the securing structure 592 for attaching straps that secure the forehead support 520 to the users head.

Figure 16A:
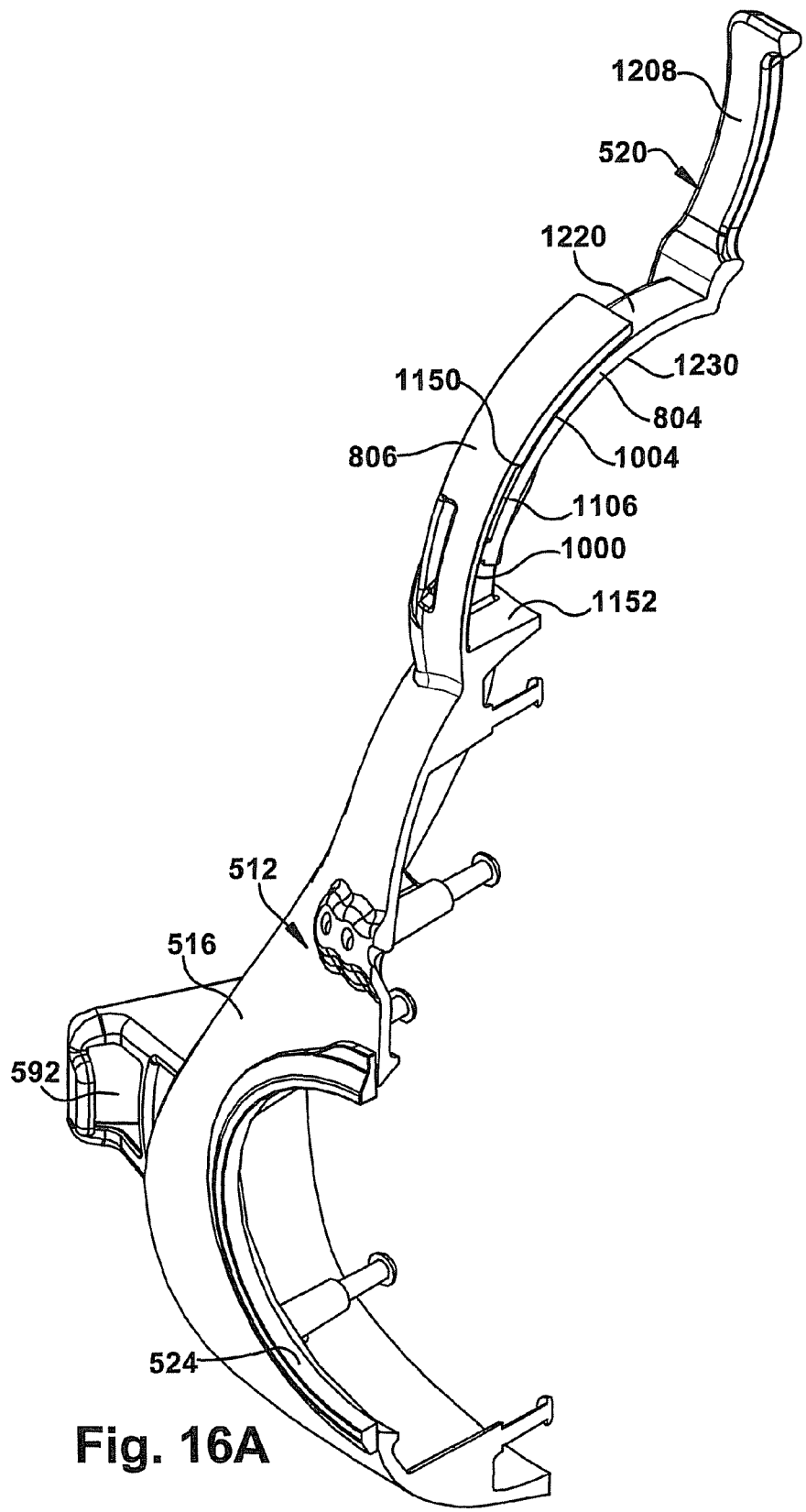
FIG. 16A is a perspective sectional view taken along the plane indicated by lines 16-16 in FIG. 15.
Figure 16B:
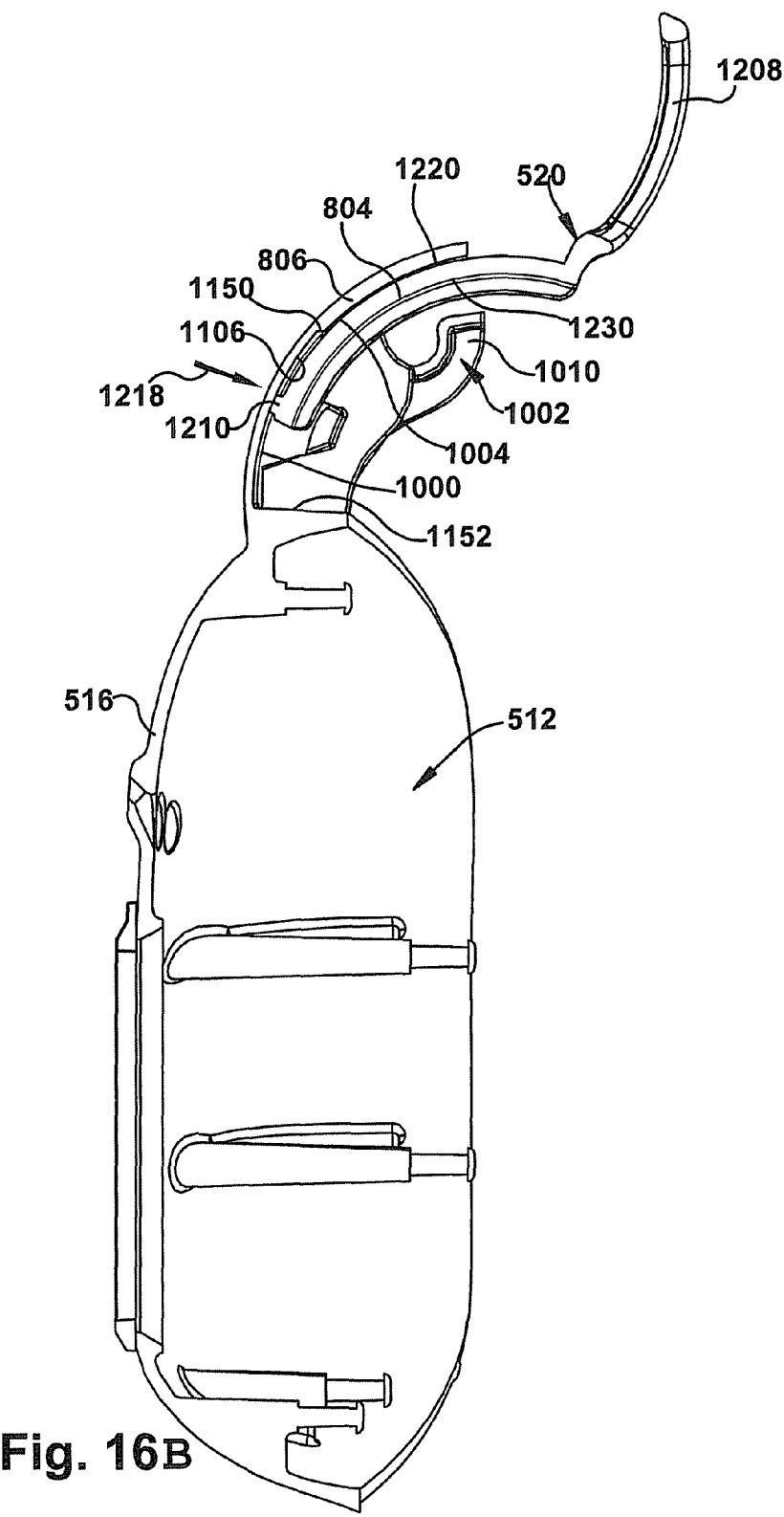
FIG. 16B is a sectional view taken along the plane indicated by lines 16-16 in FIG. 15.

Referring to FIG. 16B, the forehead support slide portion 804 has a side profile that corresponds to the path of travel of the forehead support 520 with respect to the central body 516. Referring to FIG. 12, the forehead support slide portion 804 includes a stop 1210. The stop 1210 may take a wide variety of different forms. In the illustrated embodiment, the stop 1210 is integrally formed with the forehead support slide portion 804. The stop 1210 may also be a separate member that is attached to the forehead support slide portion 804. A pair of notches 1212, are defined in the forehead support slide portion 804 on opposite sides of the stop 1210. The notches 1212, define a tongue portion 1216 that supports the stop 1210. Referring to FIGS. 12 and 16B, the tongue portion 1216 may be flexed in the direction indicated by arrow 1218 such that the stop 1210 can be moved to be flush with the surface 1220 of the forehead support slide portion 804.

Figures 13, 14A:
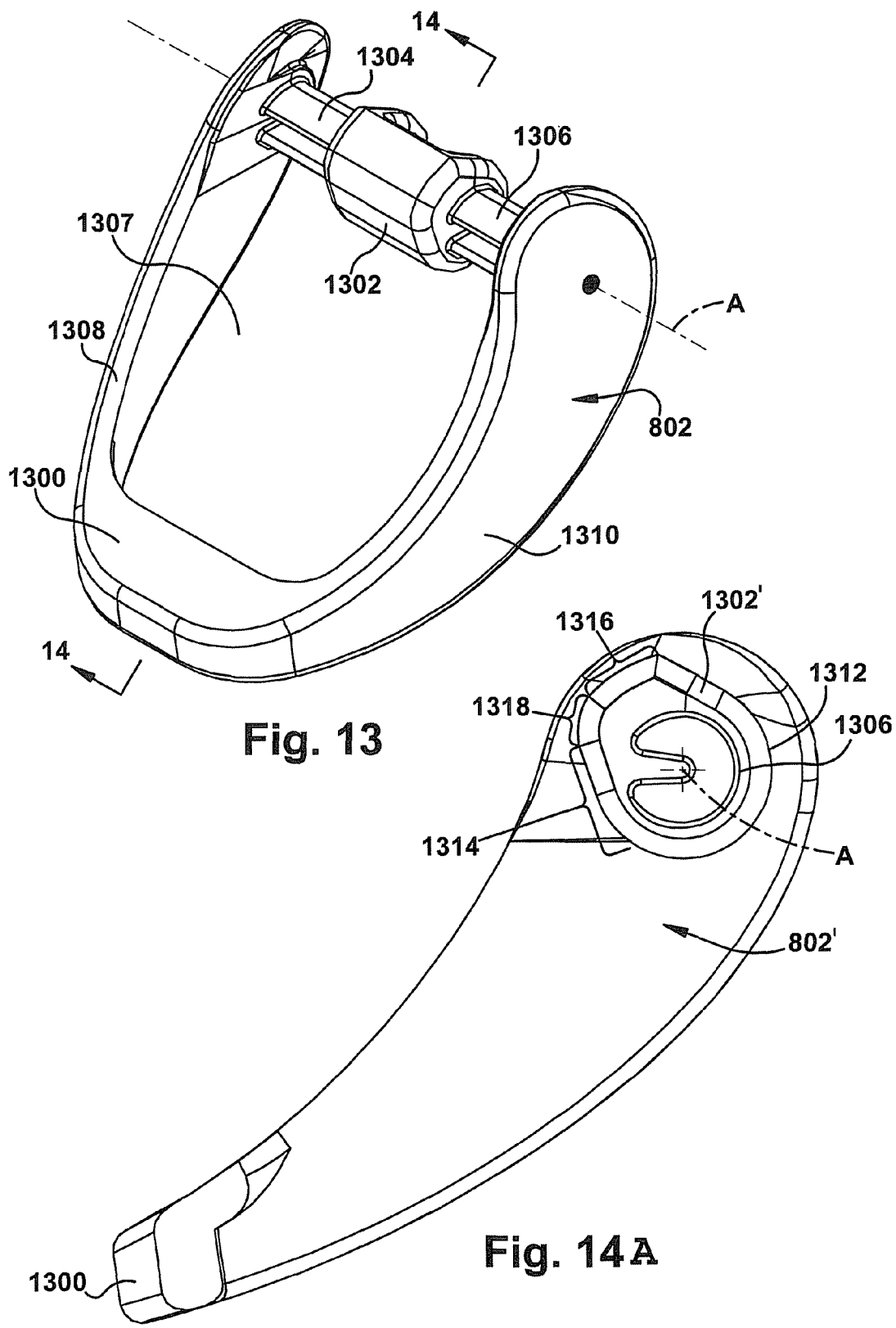
FIG. 13 is a perspective view of a cam member.
FIG. 14A is a view similar to FIG. 14 illustrating another embodiment of a cam member.
Figure 14:
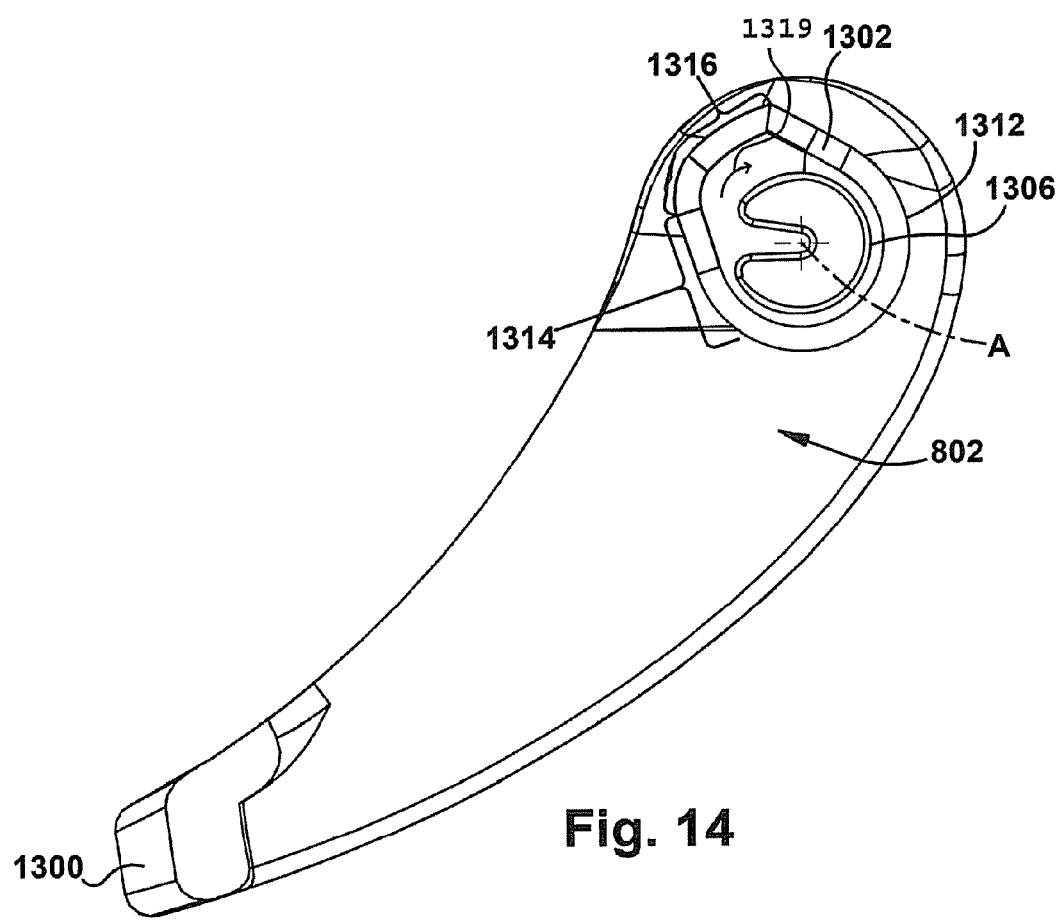
FIG. 14 is a sectional view taken along a plane indicated by the lines 14-14 in FIG. 13.
Figure 15:
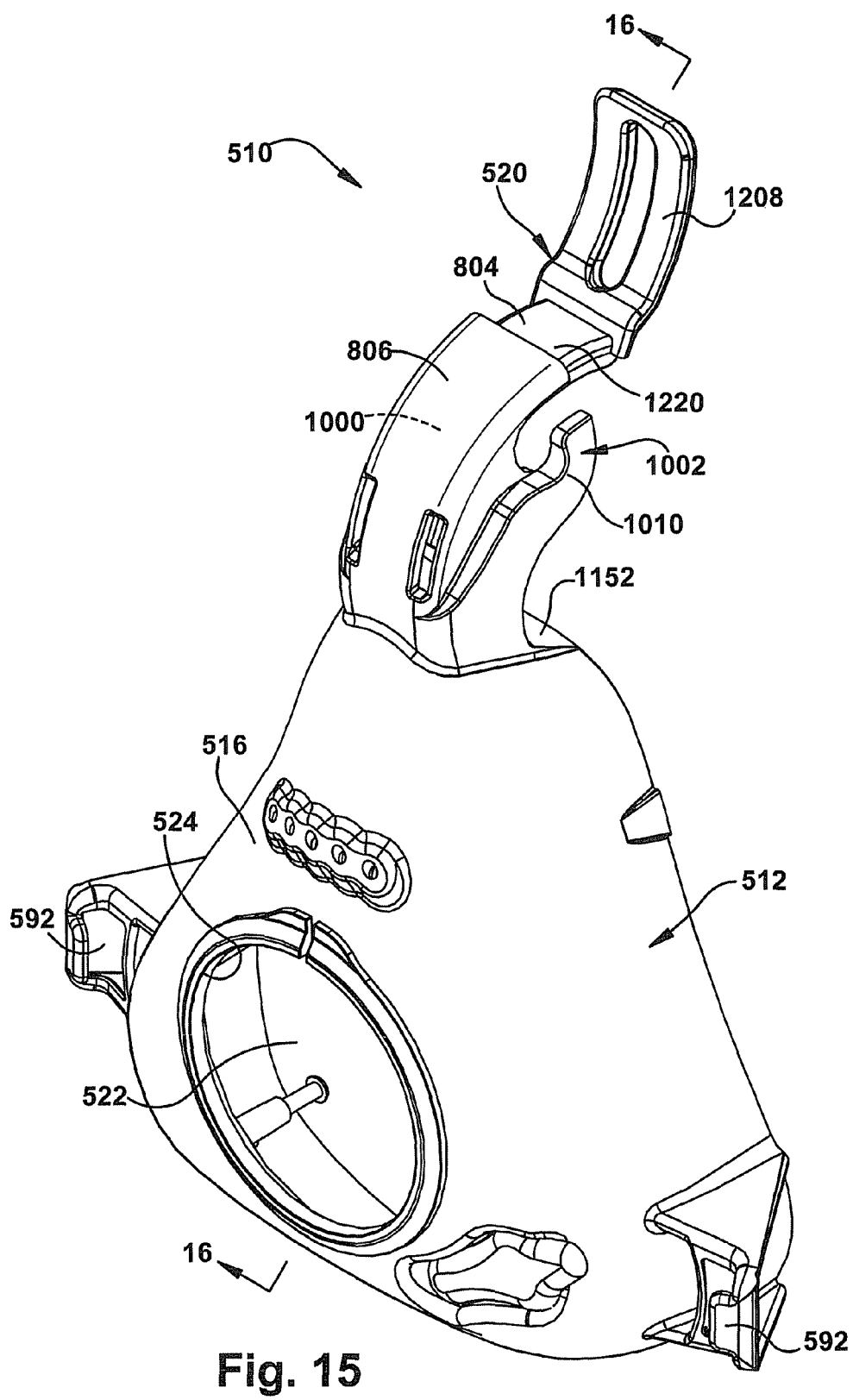
FIG. 15 is a perspective view of a forehead support assembled with a central body of a breathing mask assembly.

Referring to FIGS. 13 and 14, the cam member 802 includes a handle portion 1300, a cam portion 1302, a first shaft portion 1304, and a second shaft portion 1306. The handle portion 1300 is generally U-shaped with spaced apart arms 1308, 1310. The cam portion 1302 is disposed between the arms 1308, 1310. The cam portion 1302 is connected to the arms 1308, 1310 by the first shaft portion 1304 and the second shaft portion 1306. An opening 1307 is defined between the handle portion 1300 and the cam 1302 and shaft 1304, 1306 portions. The first and second shaft portions 1304, 1306 are generally cylindrical. Referring to FIG. 14, the shaft portions 1304, 1306 have an axis of rotation A. The cam portion 1302 has and outer surface 1312. The distance between the axis A and the outer surface 1312 varies about the periphery of the cam portion 1302. In the example illustrated by FIG. 14, the outer surface 1302 includes an unlocking portion 1314, and a locking portion 1316. A distance between the axis of rotation A and the locking portion 1316 is greater than a distance between the axis of rotation A and the unlocking portion 1314. In an exemplary embodiment, the distance from the locking portion 1316 to the axis of rotation A gradually increases in the direction indicated by arrow 1319. FIG. 14A illustrates another example of a cam member 802' with a cam portion 1302'. In the example illustrated by FIG. 14A, the cam portion 1302' includes a peak portion 1318 disposed between the locking portion 1316 and the unlocking portion 1318. A distance between the locking portion 1316 and the axis of rotation A is less than a distance between the axis of rotation A and the peak portion 1318.

Figure 22:
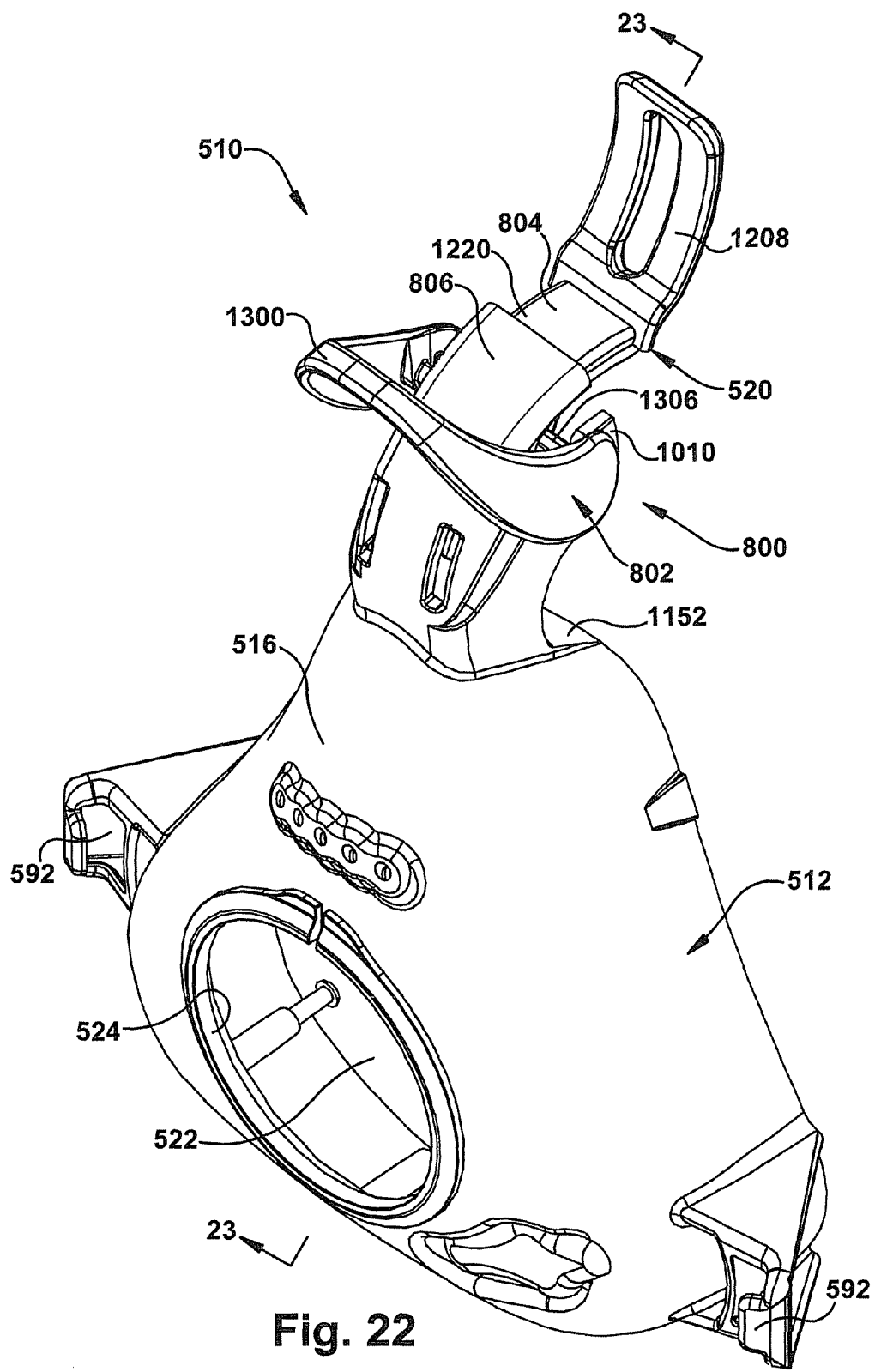
FIG. 22 is a perspective view similar to the view of FIG. 8 with a cam member in an unlocked position.
Figure 23:
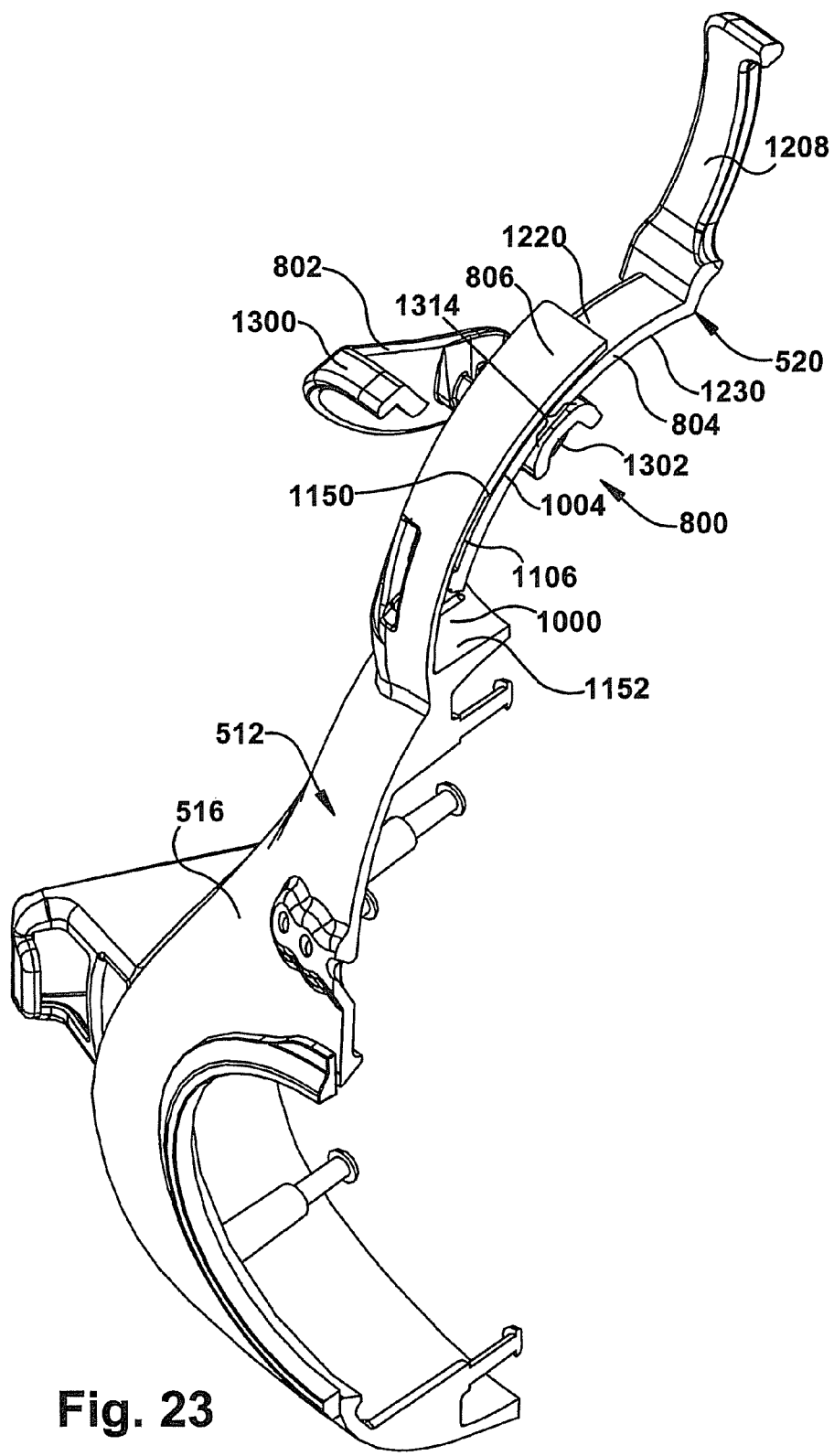
FIG. 23 is a perspective sectional view taken along the plane indicated by lines 23-23 in FIG. 22.
Figure 24:
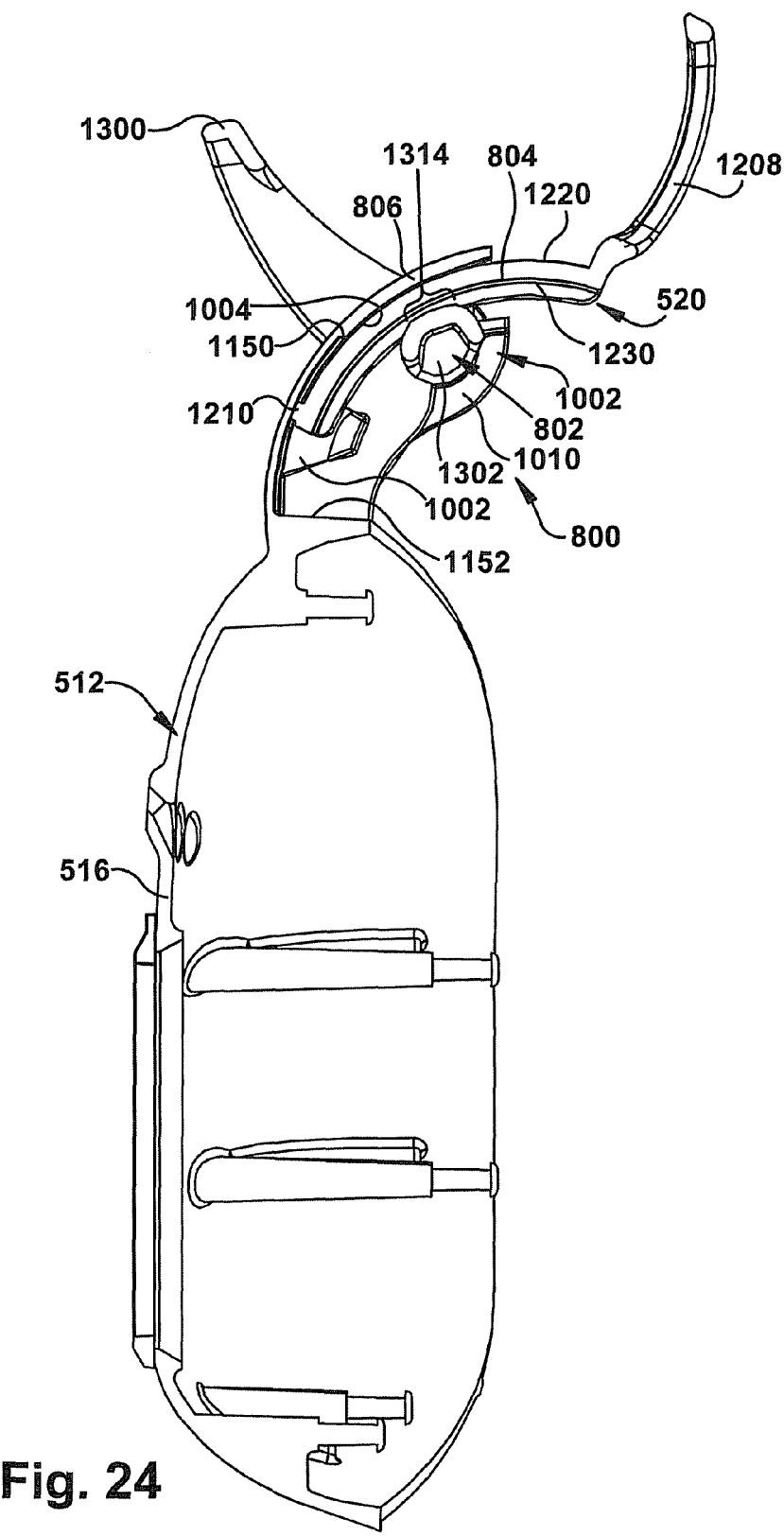
FIG. 24 is a sectional view taken along the plane indicated by lines 23-23 in FIG. 22.

Referring to FIGS. 8-10, the cam member 802 is installed onto the central body 516 by placing the shaft portions 1304, 1306 in the notches 1014 (see notch in FIG. 10, notch on opposite side is substantially the same) in the arms 1010 of the cam member mount 1002. In this position, the cam member 802 is pivotable about the axis of rotation A of the shaft portions 1304, 1306. The cam member 802 is pivoted to the unlocked position (see FIGS. 22-24) to allow the forehead support 520 to be installed in the central body. In an exemplary embodiment, the forehead support 520 is assembled with the central body 516 after the cam member 802 by positioning the cam member in the open position as shown in FIGS. 22-24. In another embodiment, the support 520 is assembled with the central body 516 before the cam member.

FIGS. 16A and 16B illustrate the forehead support 520 and the central body 516 with the cam member 802 removed to more clearly show how the forehead support 520 is assembled with the central body 516. The forehead support 520 is assembled with the central body 516 by inserting the forehead support slide portion 804 into the central body slide chamber 1000. The forehead support slide portion 804 slides in the slide chamber 1000 along a path of travel defined by the inner surface 1004 of the slide chamber and a slide surface 1220 of the forehead support slide portion 804. The stop 1210 is disposed in the stop slot 1106 (FIGS. 16A and 16B). An end 1150 of the stop slot 1106 engages the stop 1210 to limit extension of the forehead support 520 from the central body 516. A wall 1152 engages the forehead support slide portion 804 to limit retraction of the forehead support 520 into the central body 516. The stop 1210 limits movement of the forehead support 520 from a fully extended position and to a fully retracted position (fully retracted and extended positions shown in FIG. 5 in phantom). The forehead support 520 may be removed from the central body 516 by forcing the stop 1210 to become flush with the slide surface 1220 and thereby removing the stop 1210 from the stop slot 1106 (See FIG. 16B).

Figure 17:
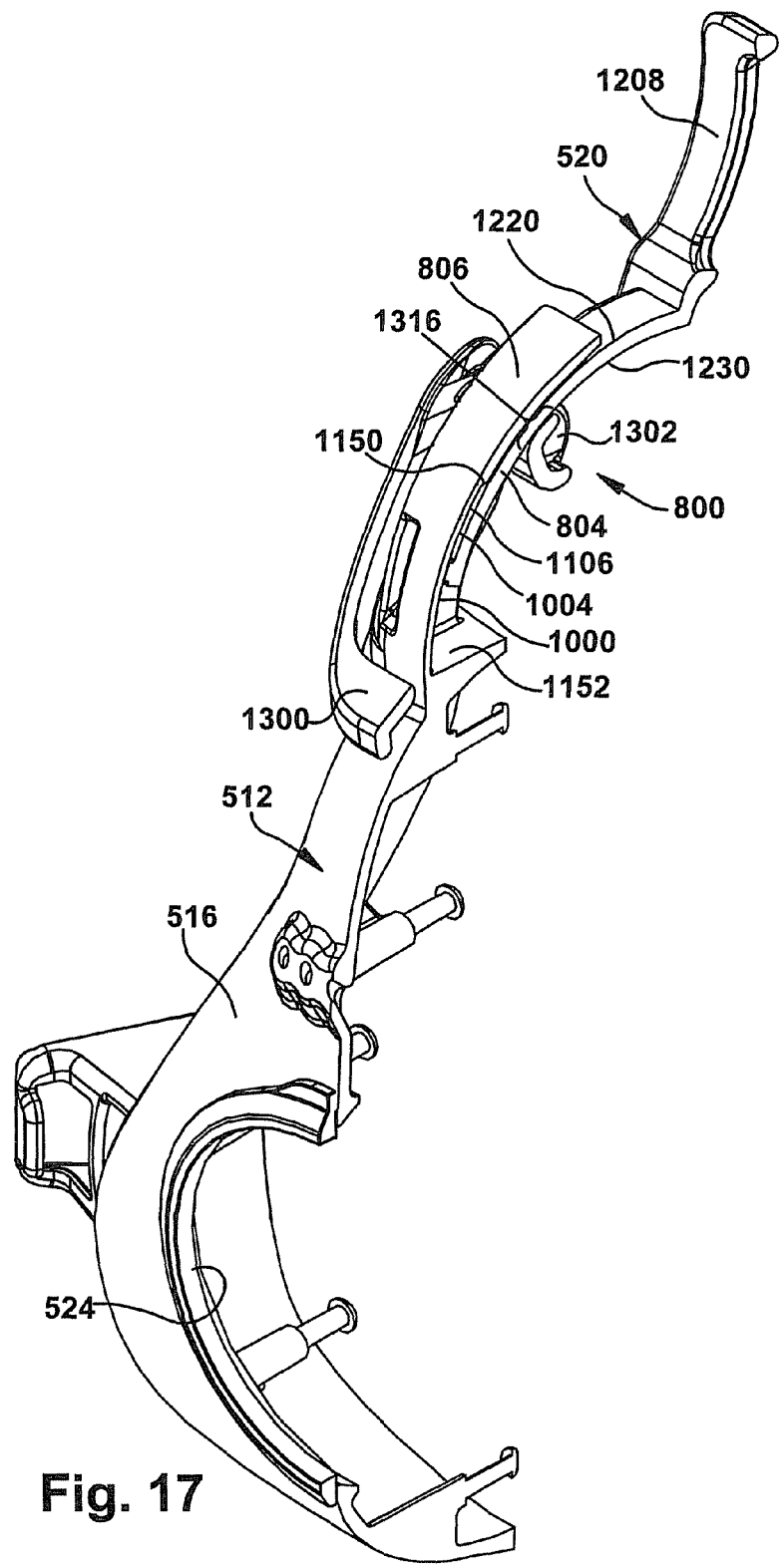
FIG. 17 is a perspective sectional view taken along the plane indicated by lines 17-17 in FIG. 8.
Figure 18:
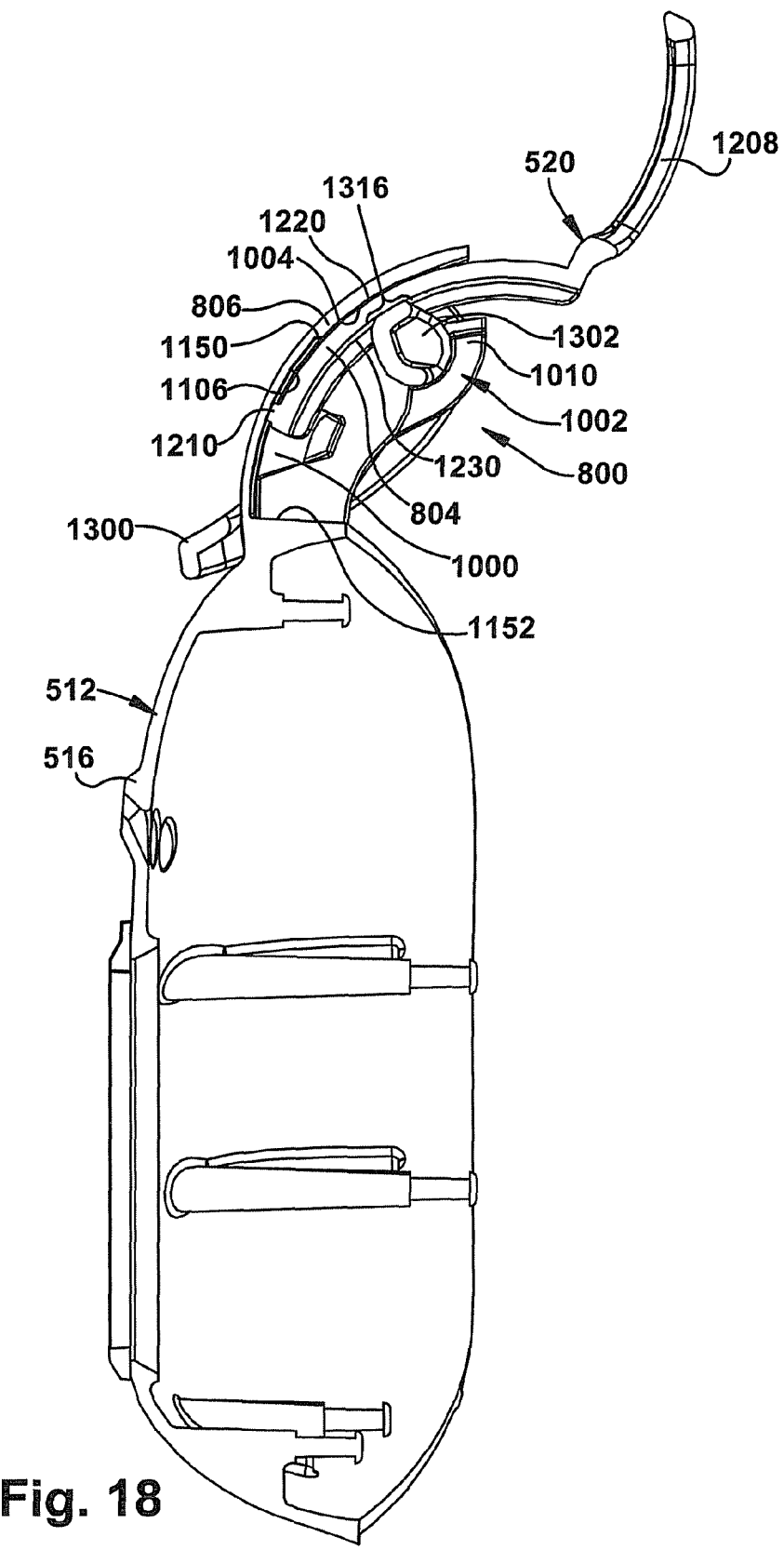
FIG. 18 is a sectional view taken along the plane indicated by lines 17-17 in FIG. 8.

Referring to FIGS. 17 and 18, when the cam member 802 is in the locked positioned, the locking portion 1316 clamps the forehead support slide portion 804 against the central body slide portion 806 to prevent relative movement between the forehead support and the central body 516.

Figure 19:
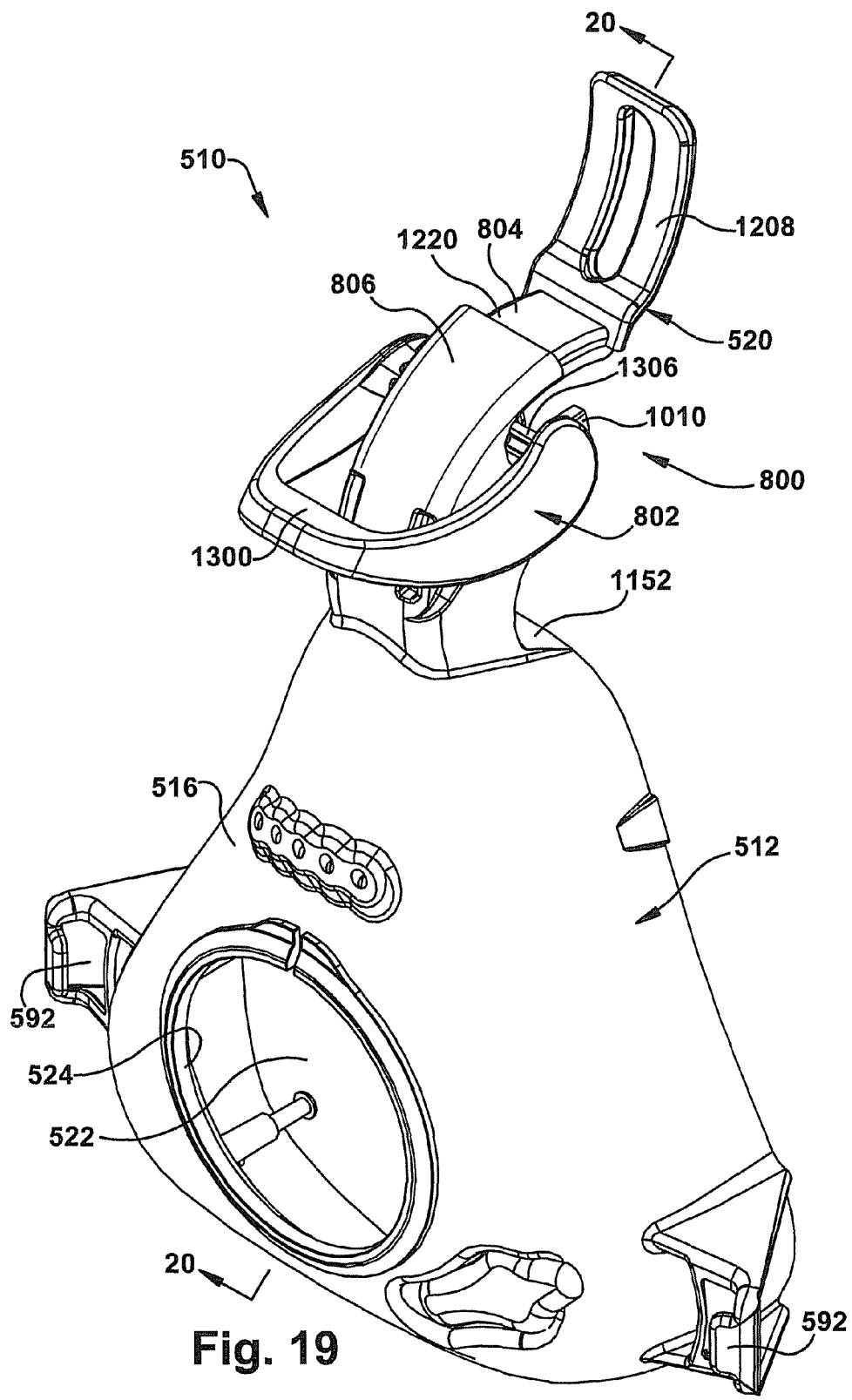
FIG. 19 is a perspective view similar to the view of FIG. 8 with a cam member in an intermediate position.
Figure 20:
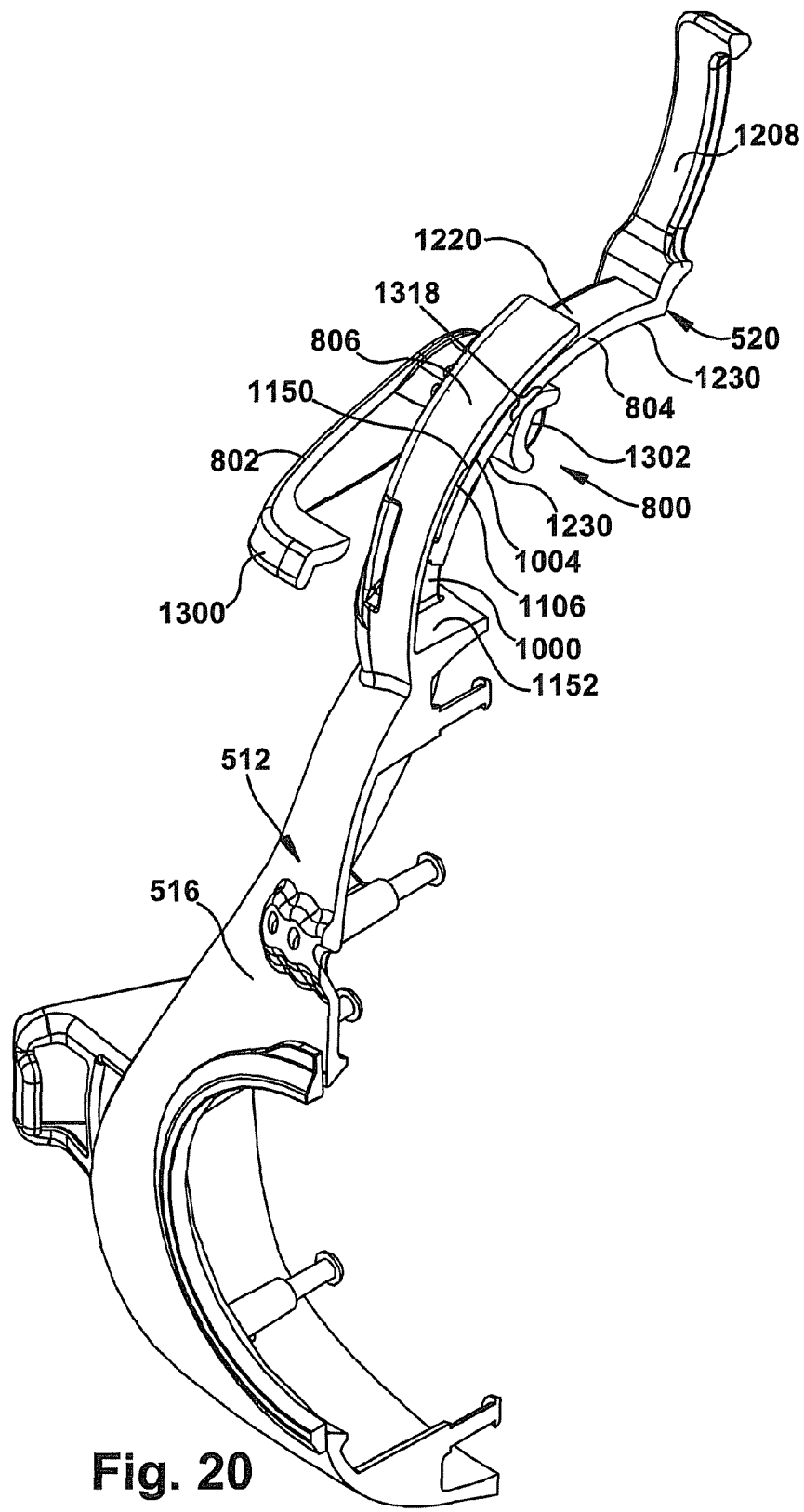
FIG. 20 is a perspective sectional view taken along the plane indicated by lines 20-20 in FIG. 19.
Figure 21:
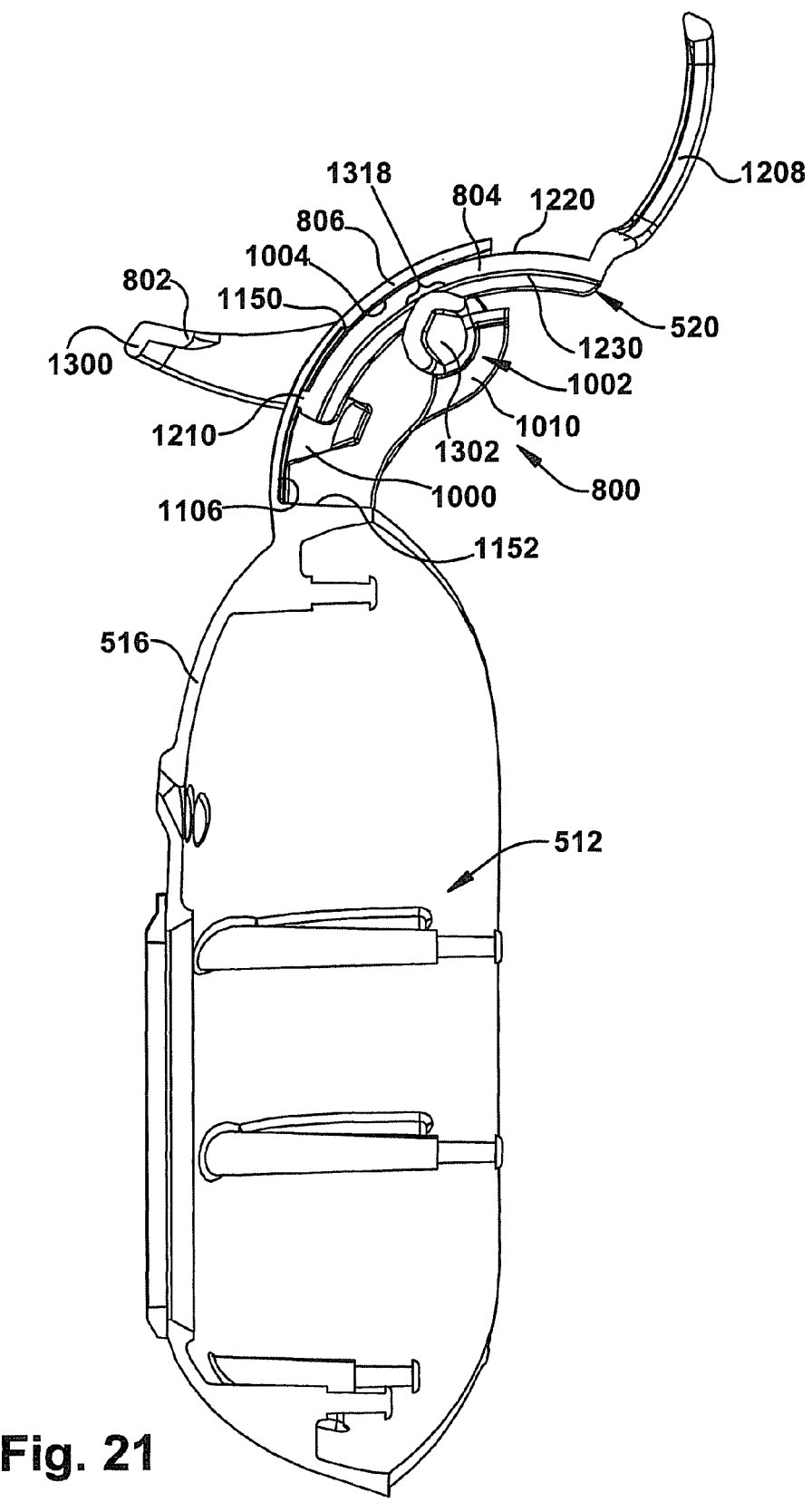
FIG. 21 is a sectional view taken along the plane indicated by lines 20-20 in FIG. 19.

FIGS. 19-21 illustrate the cam member 802 moved to an intermediate position. The cam portion 1302 engages the forehead support slide portion 804 in the intermediate position. Referring to FIG. 14, the distance from the locking portion 1316 to the central axis A increases as the handle portion 1300 is moved from the intermediate position to the locked position. As a result, additional force must be applied to the handle portion to rotate the cam member from the intermediate position to the locked position. Friction between the cam member 802 and the forehead support slide portion holds the cam member in the locked position. Force must be applied to the handle portion 1300 to overcome the frictional force and move the cam member 802 from the locked position to the unlocked position. As a result, the cam member is inhibited from moving from the locked position to the unlocked position without action by the user.

Referring to FIG. 14A, in the embodiment where the cam portion 1302' includes a peak portion 1318, a distance between the locking portion 1316 and the axis of rotation A is less then a distance between the peak portion 1318 and the axis of rotation. As a result, force must be applied to the handle portion 1300 for the cam member 802 to be moved from the locked position to the intermediate position. As a result, the cam member 802 is inhibited from moving from the locked position to the unlocked position without action by the user.

FIGS. 22-24 show the cam member 802 in an unlocked position. Referring to FIGS. 23 and 24, when the cam member 802 is in the unlocked positioned, the unlocking portion 1314 of the cam member is adjacent to, but spaced apart from, the forehead support slide portion 804. As such, the forehead support 520 can be moved with respect to the central body 516 when the cam member 802 is in the unlocked position. The forehead support 520 can be moved to a fully retracted position when the cam member 802 is unlocked. The stop 1210 would engage the wall 1152 in the fully retracted position. The cam member 802 can be moved to the locked position when the forehead support 520 is in the fully retracted position. The forehead support 520 can be moved to a fully extended position when the cam member 802 is unlocked. The stop 1210 would engage the edge 1150 of the stop slot in the fully extended position. The cam member can be moved to the locked position when the stop slot is in the fully extended position. When the cam member 802 is unlocked, the forehead support 520 can be moved to any position between the fully extended position and the fully retracted position and can then be locked in the selected position by locking the cam member.

In an exemplary embodiment, surfaces of the coupling arrangement 800 can be finished such that the position of the forehead support member 520 is not substantially changed by moving the cam member 802 from the unlocked position to the locked position. For example, the surfaces can be finished such that the friction between the slide surface 1220 of the forehead support and the further surface 1004 of the central body slide portion 806 is greater than the friction between a back surface 1230 of the forehead support slide portion 804 and the cam portion 1302. This frictional difference can be accomplished in a wide variety of different ways. In one embodiment, the components 512, 520, 802 are plastic and the cam portion 1302 is left unpolished after it is molded or machined, the back surface 1230 is textured, the slide surface 1220 is polished or textured (not smooth), and the inner surface 1004 is polished. The polished plastic surfaces of the forehead support 802 and the central body 512 stick together as the cam member is moved to the locked position.

While the present invention has been illustrated by the description of embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departing from the spirit or scope of the applicant's general inventive concept.

We claim:

1. A breathing mask comprising:
    a central body comprising an inlet aperture for receiving a delivered gas and being configured to deliver the gas for breathing by a user, the central body including at least one cam member mount arm with a notch disposed in the arm;
    a central body slide surface coupled to the central body;
    a forehead support;
    a forehead support slide surface coupled to the forehead support and slideably coupled to the central body slide surface such that the forehead support is moveable along a path of travel defined by the slide surfaces;
    a cam member that includes at least one shaft portion rotatably disposed in said notch of the at least one cam member mount arm, a handle portion connected to the shaft portion, and a cam portion connected to the shaft portion, wherein rotation of the handle portion rotates the cam portion between a first position where the cam portion engages the forehead support slide surface to clamp the forehead support slide surface and the central body slide surface together and a second position where the cam portion is disengaged from the forehead support slide surface to allow the forehead support to be moved along said path of travel with respect to the central body.

2. The breathing mask of claim 1 wherein the central body slide surface is integral with the central body.

3. The breathing mask of claim 1 wherein the forehead support slide surface is integral with the forehead support.

4. The breathing mask of claim 1 wherein the path of travel is curved.

5. The breathing mask of claim 1 wherein the central body including a pair of cam member mount arms that each include a notch.

6. The breathing mask of claim 1 wherein the central body including a pair of cam member mount arms that each include a notch and the cam member includes a pair of shaft portions disposed in the notches of the pair of mount arms.

7. The breathing mask of claim 1 wherein the forehead support includes a stop that engages a surface of the central body to limit movement forehead support along the path of travel.

8. The breathing mask of claim 7 wherein the stop is formed on a tongue that is configured to be flexed to allow the stop to disengage from the central body.

9. A method of assembling a forehead support with a breathing mask central body comprising:
    placing at least one shaft portion of a cam member in at least one notch of the central body;
    inserting a forehead support slide portion into a slide chamber of the breathing mask central body;
    moving a handle portion of the cam member to an unlocked position;
    sliding the forehead support slide portion in the central body slide chamber to adjust a position of the forehead support with respect to the breathing mask central body;
    moving the handle portion of the cam member to a locked position to fix the position of the forehead support with respect to the breathing mask central body.

10. The method of claim 9 wherein moving the handle portion of the cam member to an unlocked position comprises rotating the handle portion of the cam member to the unlocked position.

* * * * *